United States Patent [19]

Link, Jr. et al.

[11] Patent Number: 5,869,035
[45] Date of Patent: Feb. 9, 1999

[54] METHODS AND COMPOSITIONS FOR INDUCING COMPLEMENT DESTRUCTION OF TISSUE

[75] Inventors: Charles J. Link, Jr., Clive; John P. Levy, West Des Moines, both of Iowa

[73] Assignee: Human Gene Therapy Research Institute, Des Moines, Iowa

[21] Appl. No.: 748,344

[22] Filed: Nov. 13, 1996

[51] Int. Cl.$^6$ .......................... A01N 43/04; A01N 63/00; A61K 39/00; C12N 15/00
[52] U.S. Cl. .................. 424/93.7; 514/44; 424/277.1; 424/93.21; 435/240.2; 435/320.1
[58] Field of Search .................. 514/44; 424/93.7, 424/277.1, 93.21; 435/320.1, 325

[56] References Cited

U.S. PATENT DOCUMENTS 5,560,911  10/1996  Koren et al. ........................ 424/131.1
5,562,904  10/1996  Rother et al. ....................... 424/145.1

FOREIGN PATENT DOCUMENTS

WO 95/24924  9/1995  WIPO ........................... A61K 39/12

OTHER PUBLICATIONS

Kistner et al Proc. Natl. Acad. Sci. (1996) 93(20), pp. 10933–10938.

Takeuchi, Y, Dec. 1994, Type C Retrovirus Inactivation by Human Complement is Determined by Both the Viral Genome and the Producer Cell, *J. of Virology*, 68(12)8001–8007.

Squinto, S., 1995, Injectable Retroviral Particles for Human Gene Therapy, *Advanced Drug Delivery Reviews* 17 (1995) 213–226.

Rother, R., Oct. 1994, Expression of Recombinant Transmembrane CD59 in Paroxysmal Nocturnal Hemoglobinuria B Cells Confers Resistance to Human Complement, *Blood*, 85(8) 2604–2611.

Rother, R., Feb. 1994, Inhibition of Complement–Mediated Cytolysis by the Terminal Complement Inhibitor of Herpesvirus Saimiri, *J. of Virology*, 68(2) 730–737.

Rother, R., Nov. 1995, A Novel Mechanism of Retrovirus Inactivation in Human Serum Mediated by Anti–α–Galactosyl Natural Antibody, *J. of Experimental Medicine*, 182(5) 1345–1355.

Galili, U., 1993, Evolution and Pathophysiology of the Human Natural Anti–α–Galactosyl IgG (Anti–Gal) Antibody, *Springer Semin Immunopathol* 15:155–171.

Rother, R., Apr. 1995, Protection of Retroviral Vector Particles in Human Blood Through Complement Inhibition, *Human Gene Therapy* 6:429–435, Mary Ann Liebert, Inc., Publishers.

Galili, Uri, Aug. 1985, Human Natural Anti–α–Galactosyl IgG: II. The Specific Recognition of α(1→3)–linked Galactose Residues, *J. Exp. Med.* 162:573–582, The Rockefeller University Press.

Rollins, S., Mar. 1996, Retroviral Vector Producer Cell Killing in Human Serum is Mediated by Natural Antibody and Complement: Strategies for Evading the Humoral Immune Response, *Human Gene Therapy* 7:619–626, Mary Ann Liebert, Inc., Publishers.

Parker, W., Aug. 1996, Transplantation of Discordant Xenografts: A Challenge Revisited, *Immunology Today Review*; 17(8) 373–378.

Widner, Håkan, Jul. 1988, Immunological Aspects of Grafting in the Mammalian Central Nervous System. A Review and Speculative Synthesis, *Brain Research Reviews* 13:287–324.

Neethling, F., Mar. 1994, Protection of Pig Kidney (PK15) Cells from the Cytotoxic Effect of Anti–Pig Antibodies by a–Galactosyl Oligosaccharides, *Transplantation*, 57(6) 959–963.

Weisman, H., Recombinant Soluble CR1 Suppressed Complement Activation, Inflammation, and Necrosis Associated with Reperfusion of Ischemic Myocardium, *Transactions of the Association of American Physicians*, V. 103:64–72, at Washington, D.C. May 4–7, 1990.

Galili, U., (1988) The Natural Anti–Gal Antibody, the B–Like Antigen, and Human Red Cell Aging, *Blood Cells* 14:205–220 (Article); 14:221–224 (Commentary); 14:225–228 (Reply to Commentary).

Almeida, I, Apr. 1991), Complement–Mediated Lysis of Trypanosoma Cruzi Trypomastigotes by Human Anti–α–Galactosyl Antibodies, *J. of Immunology*, 147(7) 2394–2400.

Hamadeh, R., Human Natural Anti–Gal IgG Regulates Alternative Complement Pathway Activation on Bacterial Surfaces, Apr. 1992, *J. of Clinical Investigation, Inc.* 89:1223–1235.

Galili, U., Interaction Between Human Natural Anti–α–Galactosyl Immunoglobulin G and Bacteria of the Human Flora, Jul. 1988, *Infection and Immunity*, vol. 56:1730–1737.

Cosset, F., Dec. 1995, High–Titer Packaging Cells Producing Recombinant Retroviruses Resistant to Human Serum, *J. of Virology*, 69(12) 7430–7436.

Galili, U., 1995, α–Galactosyl (Galα1–3Galβ1–4GLCNAC–R) Epitopes on Human Cells: Synthesis of the Epitope on Human Red Cells by Recombinant Primate α1,3Galactosyltransferase Expressed in E.Coli, *Glycobiology*, 5(8):775–782.

Weisman, H., Soluble Human Complement Receptor Type 1: In Vivo Inhibitor of Complement Suppressing Post–Ischemic Myocardial Inflammation and Necrosis, *Science*, 249:146–150.

(List continued on next page.)

*Primary Examiner*—Lila Feisee
*Assistant Examiner*—Greetha P. Bansal
*Attorney, Agent, or Firm*—Zarley, McKee, Thomte, Voorhees & Sease

[57] ABSTRACT

The invention discloses methods and compositions for killing tumor cells in animals. Through transfer techniques, cancer cells are engineered to express an epitope which is targeted by natural antibodies causing complement destruction of transformed tumor cells that is typically associated with hyperacute xenograft rejection.

14 Claims, 5 Drawing Sheets

OTHER PUBLICATIONS

Weiler, J., May 1992, Heparin and Modified Heparin Inhibit Complement Activation In Vivo, *J. of Immunology*, 148(10) 3210–3215.

Gorelik, E., Sep. 1995, Alterations of Cell Surface Carbohydrates and Inhibition of Metastatic Property of Murine Melanomas by a1,3 Galactosyltransferase Gene Transfection, *Cancer Research*, 55:4168–4173.

Joziasse, D., Aug. 1989, Bovine α1→3–Galactosyltransferase: Isolation and Characterization of a cDNA Clone: Identification of Homologous Sequences in Human Genomic DNA, *J. of Biological Chemistry*, 264(24)14290–14297.

Russell, D., May 1995, The Effects of Human Serum and Cerebrospinal Fluid on Retroviral Vectors and Packaging Cell Lines, *Human Gene Therapy* 6:635–641, Mary Ann Liebert, Inc., Publishers.

Paulus, W., Jan. 1996, Self–Contained, Tetracycline–Regulated Retroviral Vector System for Gene Delivery to Mammalian Cells, *J. of Virology*, 70(1) 62–67.

Galili, U., Nov. 1988, Man, Apes, and Old World Monkeys Differ from Other Mammals in the Expression of a–Galactosyl Epitopes on Nucleated Cells, *J. of Biological Chemistry*, 268(33) 17755–17762.

Larsen, R., Apr. 1990, Frameshift and Nonsense Mutations in a Human Genomic Sequence Homologous to a Murine UDP–Gal:β–D–Gal(1,4)–D–GlcNAc α (1,3)–Galactosyltransferase cDNA, *J. of Biological Chemistry*, 265(12) 7055–7061.

Somerville, C., 1993, Future Directions in Transplantation: Xenotransplantation, *Kidney International*, vol. 44, Suppl. 42(1993) S–112–S121.

Leventhal, J., Prolongation of Cardiac Xenograft Survival by Depletion of Complement, *Transplantation*, 55(4) 857–866.

Pruitt, S., Feb. 1994, The Effect of Soluble Complement Receptor Type 1 on Hyperacute Rejection of Procine Xenografts, *Transplantation* 57(3) 363–370.

Galili, U., Nov. 1984, A Unique Natural Human IgG Antibody with Anti–α–Galactosyl Specificity, *J. Exp. Med.*, 160:1519–1531, The Rockefeller University Press.

Galili, U., Aug. 1991, Gene Sequences Suggest Inactivation of a–1,3–Galactosyltransferase in Catarrhines After the Divergence of Apes from Monkeys, *Proc. Natl. Acad. Sci. USA*, 88:7401–7404.

METHODS AND COMPOSITIONS FOR INDUCING COMPLEMENT DESTRUCTION OF TISSUE

FIELD OF THE INVENTION

The present invention relates to gene therapy techniques both in vivo and ex vivo for treating cancer in animals. The protocol causes induction of complement mediated destruction of tumors via transformation of tumor cells with gene sequences encoding proteins targeted by the humoral immune system.

BACKGROUND OF THE INVENTION

A primary barrier to xenotransplantation has been the essentially immediate recognition of carbohydrate epitopes present in the foreign tissue causing hyperacute xenograft rejection (HAR). The reaction begins immediately upon reperfusion, and once initiated destroys the foreign tissue within minutes to a few hours. The presence of HAR in some donor/recipient combinations while not others is postulated to be related to two primary factors, a) the binding of xenoreactive natural antibodies of the recipient to antigens or endothelial cells in the graft and b) the incompatibility of complement regulatory proteins in the transplant with the complement system of the recipient, allowing uncontrolled activation of complement. Greater than 80% of the complement-fixing natural antibodies in human serum recognize a single structure-Gal$\alpha$1–3Gal. The synthesis of Gal$\alpha$1–3Gal is catalyzed by the enzyme $\alpha$1,3 galactosyl transferase.

No such recognition and destruction system exists for recognition of neoplastic cells and has remained the primary hurdle towards identification of an effective strategy for destruction of these cells. The ability to distinguish neoplastic from normal cells on the basis of proliferative behavior has proven limited, and has inspired a search for biochemical characteristics of neoplastic cells that are tumor specific rather than proliferation specific. Unfortunately current molecular genetic studies have failed to support the expectation that such characteristics are a consistent feature of neoplastic cells. Rather these studies suggest that the neoplastic state can be explained without postulating tumor specific functions, but merely the operation of normal proliferation-specific functions at abnormal levels, as a result of changes (sometimes minimal) in the structure of growth-regulatory genes or changes in their number or chromosomal environment. This conclusion suggests that a continued search for highly specific attributes of neoplastic cells cannot be relied upon for a general solution to the problems of cancer therapy. Major reductions in the lethality of cancer will require alternative approaches that do not depend on the natural occurrence of such attributes.

One alternative strategy entails the artificial creation of differences between normal and neoplastic cells through prophylactic use of gene insertion techniques. In other words, manufacturing biochemical differences which can be exploited to systematically and specifically target neoplastic cells for destruction. Gene insertion protocols are used to artificially manufacture biochemical differences in target tumor cells which are then exploited to selectively kill these cells. One system which has received much attention to date is the Herpes Simplex Virus Ganciclovir System.

Transformation of tumor cells with a gene encoding Herpes Simplex Virus thymidine kinase and subsequent treatment with anti-viral agents such as ganciclovir has been previously accomplished and has proven to be operable in vivo both in animals and in humans. See "Gene Therapy for the Treatment of Recurrent Pediatric Malignant Astrocytomas With In Vivo Tumor Transduction With Herpes Simplex Thymidine Kinase Gene/Ganciclovir System", Raffel, C et al., *Human Gene Therapy* 5 (7) p. 863–90, July 1994.

It is an object of this invention to introduce biochemical differences to tumor cells to allow for their selective killing via a complement mediated, xenoreactive natural antibody immune response.

It is a further object of this invention to provide compositions and methods for selectively killing tumor cells by complement destruction, through regulated expression of $\alpha$1,3 galactosyl transferase.

It is a further object of the invention to provide compositions and methods for introduction of heterologous genes to tumor cells.

Other objects of the invention will become apparent from the description of the invention which follows.

SUMMARY OF THE INVENTION

This invention relates to methods and compositions for selectively targeting and killing cells. Through gene therapy protocols and techniques the cells such as tumor cells are engineered to express an epitope that activates xenoreactive antibodies initiating the complement cascade, traditionally associated with hyperactive xenograft rejection. Expression of the epitope in tumor cells leads to their immediate destruction within a few hours upon exposure to human serum.

According to the invention a polynucleotide sequence which encodes upon expression $\alpha$1,3 galactosyl transferase is introduced to cells the destruction of which is desirable. The sequence is introduced through a gene transfer vehicle which can comprise a vector, a plasmid or vector producer cells which produce active viral particles. These gene transfer vehicles transform the tumor cells, and cause expression of foreign genetic material inserted therein. The resulting gene product catalyzes the synthesis of the Gal$\alpha$1–3Gal epitope, a highly reactive epitope, with over 80% of complement fixing natural antibodies recognizing this epitope.

DETAILED DESCRIPTION OF THE INVENTION

Figure 1:
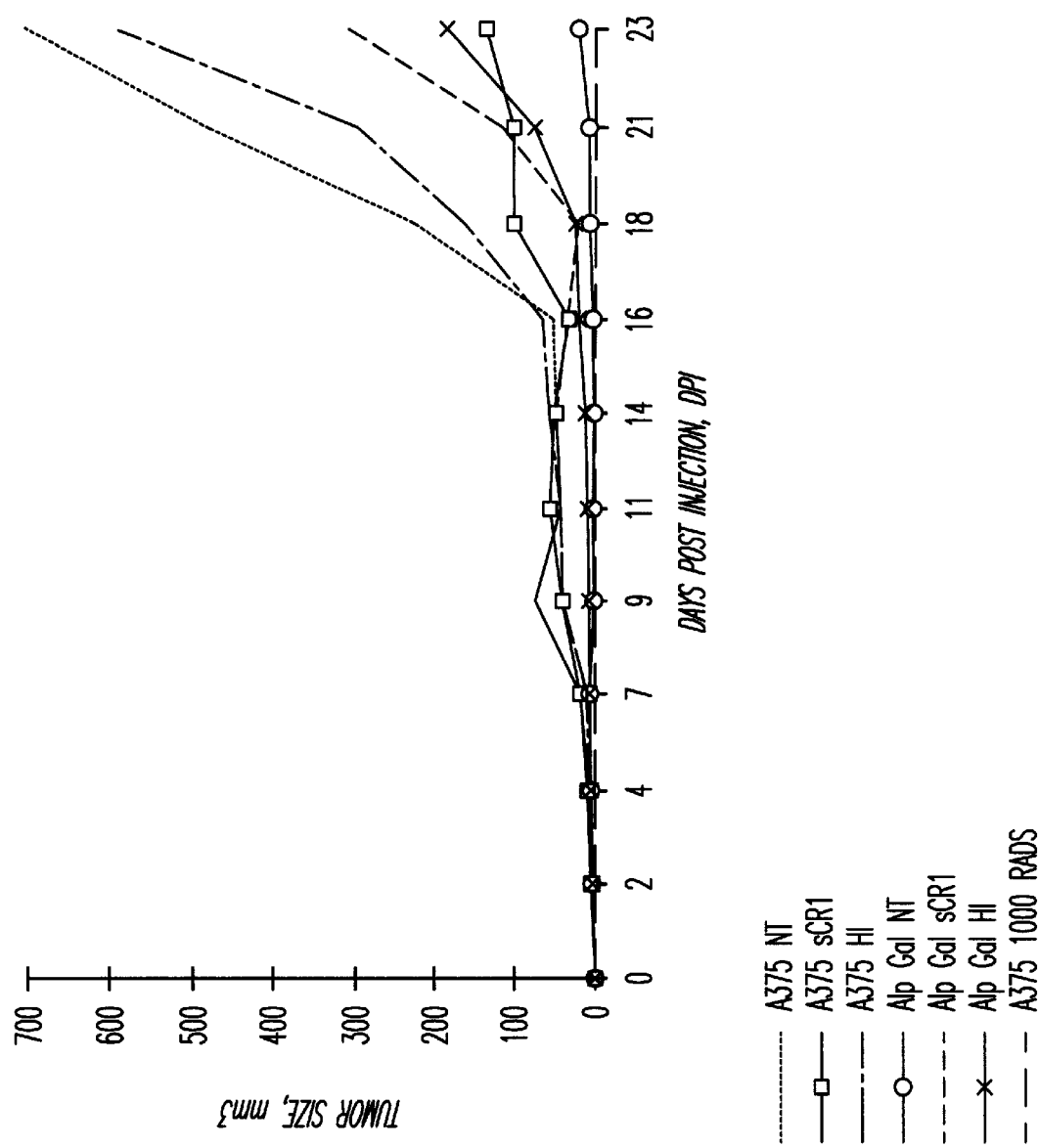
FIG. 1 is a graph depicting the effects of $\alpha$(1,3)GT expression on in vivo tumor growth. As a positive control for tumor killing one group of animals received A375 irradiated with 1000 rads. A375 nontransfected tumor cell; Alp Gal: A375 tumor cells transfected with $\alpha$1,3GT clone 7; NT: no treatment; sCR1: treatment with 25 $\mu$g/ml sCR1 for 30 minutes; HI; heat inactivated. Five animals were injected subcutaneously with 1×10$^7$ cells in each group.

Antibodies produced in humans as a result of specific vaccination or infectious disease comprise only a small portion of the bulk of the IgG molecules circulating in the blood stream. A large proportion of circulating IgG molecules are synthesized as a result of immune reactivity to naturally occurring antigens, to which the immune system is constantly exposed. Most of the known high titer natural antibodies display anti-carbohydrate specificity. These anti-carbohydrate antibodies are constantly produced as an immune response to normal gastrointestinal or pulmonary flora that contain bacteria bearing such antigenic epitopes.

One such epitope, the α galactosyl epitope is a glycosidic structure that has been identified on the surface of cells from a mammalian species excluding old world primates. The α galactosyl epitope is a "forbidden" antigen in humans since cells expressing this carbohydrate structure would be effected by anti-gal. Anti-gal, the human natural antibody interacts specifically with the mammalian carbohydrate structure galα1–3galβ1–4GlcNAc-R, the α galactosyl epitope. This antibody constitutes approximately 1% of circulating IgG in human serum and is produced upon stimulation by 1% of the circulating β lymphocytes. Anti-gal is also present as IgA antibodies and body secretions such as saliva, milk and colostrum. The antigenic source for the constant production of anti-gal seems to be the α galactosyl-like epitopes found on many bacteria of the gastri-intestinal flora. Whereas anti-gal is abundant in humans, apes and old world monkeys, it is absent from new world monkeys, Prosimians and non-primate mammals. The latter group of species produces, however, large amounts of α galactosyl epitopes (greater than $10^6$ epitopes per cell).

The enzyme α1–3 galactosyl transferase (α1,3 GT) catalyzes the synthesis of α galactosyl epitopes in the Golgi apparatus of cells from various non-primate mammals by the following reaction:

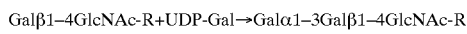

Galβ1–4GlcNAc-R+UDP-Gal→Galα1–3Galβ1–4GlcNAc-R

This enzyme was found to be active in new world monkeys but not in old world monkeys and humans. The α1,3 GT cDNA has been cloned from bovine and murine cDNA libraries. Larson, R. D. et al. (1989) "Isolation of a cDNA Encoding Murine UDP galactose; βD-galactosyl-1, 4-N Acetol-D-Glucosamine α1–3 Galactosyl Transferase: Expression Cloning by Gene Transfer", PNAS, USA 86:8227; and Joziasse, D. H. et al., (1989) "Bovine α1–3 Galactosyl Transferase: Isolation and Characterization of a cDNA Clone, Identification of Homologous Sequences in Human Genomic DNA", *J. Biol Chem* 264:14290.

The gene is present in the human genome, although no transcription has been detected. Instead, two frame shift mutations were found (deletions generating premature stop codons) in the human exons encoding the enzyme. See generally, Galili, Uri "Evolution in Pathophysiology of the Human Natural Anti-α-Galactosyl IgG(anti-Gal) Antibody, Springer Semin *Immunopathol* (1993) 15:155–171.

In humans the reaction to the presence of this epitope is swift and certain resulting in destruction of foreign tissues in minutes to hours.

The invention in one embodiment thus comprises the transformation of tumor cells with a polynucleotide which will create an α galactosyl epitope on the tumor cells. One embodiment of the invention comprises transformation of tumor cells with a nucleotide sequence which encodes upon expression, the enzyme α1,3 galactosyl transferase (α1,3 GT). The α1,3 GT cDNA has been cloned from bovine and murine cDNA libraries. Larson, R. D. et al. (1989) "Isolation of a cDNA Encoding Murine UDP galactose; βD-galactosyl-1, 4-N Acetol-D-Glucosamine α1–3 Galactosyl Transferase: Expression Cloning by Gene Transfer", PNAS, USA 86:8227; and Joziasse, D. H. et al., (1989) "Bovine α1–3 Galactosyl Transferase: Isolation and Characterization of a cDNA Clone, Identification of Homologous Sequences in Human Genomic DNA", *J. Biol Chem* 264:14290.

Yet another tumor cell embodiment involves ex vivo purging of harvested bone marrow through selective expression of the α1,3 gene under control of tumor specific promoter. Such promoters are known to those of skill in the art. See Example 17 for a list of examples of such suitable promoters. Bone marrow cells contaminated with tumor cells are transformed to contain the α1,3 gene, which is expressed in tumor cells. The selective ex vivo expression of these cells leads to specific destruction of tumor cells when resuspended in human serum.

In accordance with an aspect of the present invention, there is provided a method of treating a tumor in a human host. The method comprises transducing tumor cells in vivo, ex vivo or in vitro with a polynucleotide acid (DNA or RNA) sequence encoding an agent which encodes a protein causing the expression of an active α galactosyl epitope which is then capable of inducing the destruction of the tumor cells upon expression of the nucleic acid sequence encoding the agent and subsequent complement activation.

The nucleic acid sequence which encodes the agent which is capable of inducing destruction of tumor cells is contained in an appropriate expression vehicle which transduces the tumor cells. Such expression vehicles include, but are not limited to, eukaryotic vectors, prokaryotic vectors (such as, for example, bacterial vectors), and viral vectors.

In one embodiment, the expression vector is a viral vector. Viral vectors which may be employed include, but are not limited to, retroviral vectors, adenovirus vectors, Herpes virus vectors, and adeno-associated virus vectors, or DNA conjugates.

In a preferred embodiment, a packaging cell line is transduced with a viral vector containing the nucleic acid sequence encoding the agent which induces the destruction of the tumor cells by complement activation upon expression of the nucleic acid sequence encoding the agent to form a producer cell line including the viral vector. The producer cells then may be administered to the tumor, whereby the producer cells generate viral particles capable of transducing the tumor cells, alternatively the viral particles can be harvested from supernatant of the cells and these can be directly administered.

Traditionally, the viral vector is a retroviral or adenoviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.,* 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point.

In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques,* 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters.

In a preferred embodiment the invention comprises an inducible promoter so that α1,3 GT expression is minimized until a sufficient number of cells are transfected and to minimize cytotoxicity. One such promoter is the tetracycline-controlled transactivator (tTA)-responsive promoter (tet system), a prokaryotic inducible promotor system which has been adapted for use in mammalian cells. The tet system was organized within a retroviral vector so that high levels of constitutively-produced tTA mRNA function not only for production of tTA protein but also the decreased basal expression of the response unit by antisense inhibition. See, Paulus, W. et al., "Self-Contained, Tetracycline-Regulated Retroviral Vector System for Gene Delivery to Mammalian Cells", *J of Virology,* January. 1996, Vol. 70, No. 1, pp. 62–67.

The selection of a suitable promoter will be apparent to those skilled in the art from the teachings contained herein.

The vector then is employed to transduce a packaging cell line to form a producer cell line. Examples of packaging cells which may be transfected include, but are not limited to the PE501, PA317, ψ2, ψ-AM, PA12, T19-14X, VT-19-17-H2, ψCRE, ψCRIP, GP+E-86, GP+envAM12, and DAN cell lines. The vector containing the nucleic acid sequence encoding the agent which is capable of providing for the destruction of the tumor cells upon expression of the nucleic acid sequence encoding the agent, and activation of the complement cascade may transduce the packaging cells through any means known in the art. Such means include, but are not limited to, electroporation, the use of liposomes, and CaPO$_4$ precipitation.

The producer cells then are administered directly to or adjacent to the tumor in an amount effective to destroy the growth of the tumor upon exposure to human serum. In general, the producer cells are administered in an amount tolerated by the patient, it is desirable to inject as many producer cells as possible. The exact amount of producer cells to be administered is dependent upon various factors, including but not limited to, the type of the tumor and the size of the tumor.

In general, the producer cells are administered directly to or adjacent to the tumor by injection. The producer cells are administered in combination with a pharmaceutically acceptable carrier suitable for administration to a patient. The carrier may be a liquid carrier such as, for example, a saline solution.

Upon administration of the producer cells to the tumor, the producer cells generate viral particles. The viral particles then transduce the surrounding tumor cells. Because tumor cells, and in particular cancerous tumor cells, in general are actively replicating cells, the retroviral particle would be integrated into and expressed preferentially or exclusively in the tumor cells as opposed to normal cells.

It is important to note for purposes of this invention that type C retrovirus express the α-galactosyl epitope on the retroviral envelope. The α-galactosyl epitope is expressed on the surface of amphotropic and ecotropic retroviruses localized to the retroviral envelope glycoprotein gp70. Down regulation of this epitope on the surface of murine retroviral particle producer cells rendered them as well as the particles liberated from these cells resistance to an activation by human serum complement. Thus in a preferred embodiment, the vectors and vector producer cells are treated to down regulate the expression of the α-galactosyl epitope until transfection is complete.

The mechanism of inactivation of murine type C amphotropic and ecotropic retroviral particles by human serum complement requires that the retrovirus originate from cells that encode a functional -α1–3-galactosyl transferase (i.e., cells derived from mammalian species other than old world primates), and is dependent on both the viral genome and producer cell type. Takeuchi, Y. et al. (1994) "Type C Retrovirus Inactivation By Human Complement Is Determined By Both The Viral Genome And The Producer Cell", J. Virol. 68:8001–8007.

See Rother, Russell P. et al., "A Novel Mechanism Of Retrovirus Inactivation In Human Serum Mediated By The Anti-α-Galactosyl Natural Antibody", J. of Experimental Medicine, Vol. 182:5 Nov. 1, 1995, pp. 1345–1355. The presence of the α-galactosyl epitope site may be screened for using in vitro titer assays involving exposure of the viral vectors to human serum as disclosed in the methods of Rother et al, "A Novel Mechanism Of Retrovirus Inactivation In Human Serum Mediated By The Anti-α-Galactosyl Natural Antibody", J. of Experimental Medicine, Vol. 182:5 Nov. 1, 1995, pp. 1345–1355 incorporated herein by reference.

Thus in a preferred embodiment when these types of retroviruses are used as either vectors or vector producer cells, the α-galactosyl epitope is inhibited or removed.

Pretreatment of human serum with functionally blocking mabs that target the terminal complement components is one method to effectively protect retroviral particles from inactivation. Rother et al., Human Gene Therapy, 6:429–435 (April 1995). Further, retroviral particles can be protected from complement mediated inactivation by the addition of soluble gal α1–3 Gal. Finally generation of retroviral vector packaging cell lines and vectors through engineering techniques to introduce inactivating mutation or deletion of sequences can be employed according to the methods generally disclosed in Maniantas et al, "Molecular Cloning, A Lab Manual", Cold Spring Harbor Press 1992. Similarly addition of sCR1, Lovenox and heparin inhibit complement mediated destruction. sCR1 is a soluble form of complement receptor 1 effectively binds complement and prevents the attach complex.

Down regulation of the epitope has been accomplished in PA317VPC and resulted in production of retroviral particles that are resistant to human complement. Other potential strategies include use of packaging cheloids derived from old world primates or certain Chinese hamster ovary or baby hamster kidney cell lines all of which do not express the α-galactosyl epitope. Rother et al. Supra.

CD59 is a human terminal complement regulatory protein. In yet another protocol, a CD59 homolog from the squirrel monkey was cloned, and cells stably expressing CD59 were protected from complement mediated lysis by human serum. Rather et al., "Inhibition of Complement Mediated Cytolysis by the Terminal Complement Inhibitor of Herpes Virus Saimiri", J. of Virology, Feb. 1994, pp. 730–737, Vol. 68, No. 2. Rather et al., Vol. 84, No. 8 (Oct. 15, 1994) pp. 2604–2611, "Express of Recombinant Transmembrane CD59 in Paroxysmal Nocturnal Hemoglobinuria B Cells Confers Resistance to Human Complement".

In a preferred embodiment the invention comprises a viral vector which commonly infects humans and packaging cell line which is human based. For example vectors derived from viruses which commonly infect humans such as Herpes Virus, Epstein Barr Virus, may be used which do not express an active α-galactosyl envelope.

In a most preferred embodiment the vector comprises a Herpes Simplex Virus plasmid vector. Herpes simplex virus type-1 (HSV-1) has been demonstrated as a potential useful gene delivery vector system for gene therapy, Glorioso, J. C., "Development of Herpes Simplex Virus Vectors for Gene Transfer to the Central Nervous System. Gene Therapeutics: Methods and Applications of Direct Gene Transfer", Jon A. Wolff, Editor, 1994 Birkhauser Boston, 281–302; Kennedy, P. G., "The Use of Herpes Simplex Virus Vectors for Gene Therapy in Neurological Diseases", O J Med, Nov. 1993, 86(11):697–702; Latchman, D. S., "Herpes Simplex Virus Vectors for Gene Therapy", Mol Biotechnol, Oct. 1994, 2(2):179–95.

HSV-1 vectors have been used for transfer of genes to muscle. Huard, J., "Herpes Simplex Virus Type 1 Vector Mediated Gene Transfer to Muscle", Gene Therapy, 1995, 2, 385–392; and brain, Kaplitt, M. G., "Preproenkephalin Promoter Yields Region-Specific and Long-Term Expression in Adult Brain After Direct In Vivo Gene Transfer Via a Defective Herpes Simplex Viral Vector", Proc Natl Acad Sci USA, Sep. 13, 1994, 91(19):8979–83, and have been used for murine brain tumor treatment, Boviatsis, E. J., "Long-Term Survival of Rats Harboring Brain Neoplasms Treated With Ganciclovir and a Herpes Simplex Virus Vector That Retains an Intact Thymidine Kinase Gene", *Cancer Res, Nov.* 15, 1994, 54(22):5745–51; Mineta, T., "Treatment of Malignant Gliomas Using Ganciclovir-Hypersensitive, Ribonucleotide Reductase-Deficient Herpes Simplex Viral Mutant", *Cancer Res,* Aug. 1, 1994, 54(15) :3963–6.

Helper virus dependent mini-viral vectors have been developed for easier operation and their capacity for larger insertion (up to 140 kb), Geller, Al, "An Efficient Deletion Mutant Packaging System for Defective Herpes Simplex Virus Vectors: Potential Applications to Human Gene Therapy and Neuronal Physiology", *Proc Natl Acad Sci USA,* November 1990, 87(22):8950–4; Frenkel, N., "The Herpes Simplex Virus Amplicon: A Versatile Defective Virus Vector", *Gene Therapy. l. Supplement* 1, 1994. Replication incompetent HSV amplicons have been constructed in the art, one example is the pHSVlac vector by Geller et al, *Science,* Vol. 241, September 1988, incorporated herein by reference. These HSV amplicons contain large deletions of the HSV genome to provide space for insertion of exogenous DNA. Typically they comprise the HSV-1 packaging site, the HSV-1 "ori S" replication site and the IE 4/5 promoter sequence. These virions are dependent on a helper virus for propagation.

Primarily two types of mutant helper viruses have been developed to minimize recombination. Other complementary HSV helper virus systems are contemplated herein and are within the scope of those of skill in the art. One such system which has been developed is a temperature-sensitive mutant. An HSV temperature-sensitive (TS) mutant has been developed with a TS mutation in the IE3 gene. Davison et al, 1984, *J. Gen. Virol.,* 65:859–863. Consequently this virus has an IE phenotype, does not replicate DNA, does not significantly alter cellular physiology, and does not produce progeny virus at 37° C. Virus is grown at the permissive temperature of 37° C. TS mutants however have had a tendency to revert to wild type.

In contrast a second helper virus system is a deletion mutant with the majority of the IE3 gene simply deleted. These do not revert to wild type. Therefore HSV-1 vectors packaged using a deletion mutant as helper virus is the most preferred helper virus of the invention. See for example Patterson et al., 1990, *J. Gen. Virol.,* 71:1775–1783. Other replication incompetent helper viruses can be used and one of skill in the art will appreciate that other mutations in the IE genes or other genes which result in a replication incompetent helper virus which will provide the appropriate replication and expression functions and which are coordinated with the helper cell line and vector are contemplated within this invention. Any cell line can be used for this step so long as it is capable of expressing the IE3 or replication dependent gene, or obtaining a helper cell line which has already been transformed and is commercially available. Any cell line can be used by introducing pHE and the plasmid containing the IE3 gene simultaneously. Next, the vector is delivered to the helper cell line by electroporation, calcium phosphate DNA transfection or any other suitable method. Any cell line can be used by introducing pHE and the plasmid containing the IE3 gene simultaneously. The cells are next infected with a helper virus IE3 deletion mutant or other corresponding deletion mutant which is replication incompetent. The IE3 gene or other such gene in the helper cell line complements the helper virus resulting in a productive HSV-1 infection and the resulting virus stock consists of HSV-1 particles containing either vector DNA or helper virus DNA, all of which are replication incompetent. Further information about helper cell lines and the methodology is disclosed in Geller et al., *PNAS,* 87:8950–8954, November 1990, "An Efficient Deletion Mutant Packaging System for Defective Herpes Simplex Virus Vectors: Potential Applications to Human Gene Therapy and Neuronal Physiology". The invention comprises a HSV mini vector which combines a replication incompetent HSV amplicon with other viral sequences such as those from Epstein-Barr virus, human papillomavirus, or bovine papillomavirus type 1 which allow the vector to be maintained in the cell in episomal form achieving a 10 times greater titre, and a very large DNA insert capacity.

Figure 5:
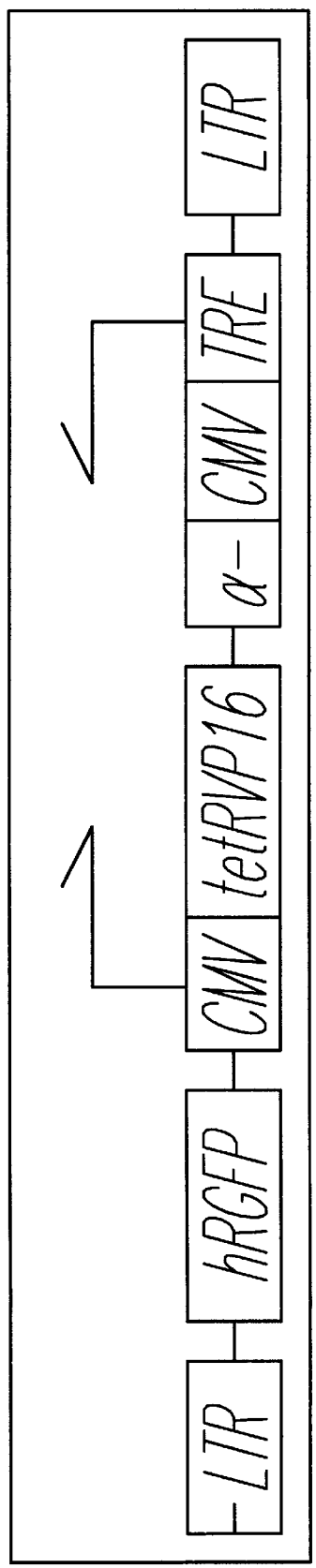
FIG. 5 is a depiction of proposed retroviral vector.

One embodiment of the present invention involves a helper virus-dependent mini-viral vector comprising: (a) the HSV-1 "a" sequence for the package/cleavage signal and an "ori S" replication origin for the replication packaging of the plasmid (in response to signals to replicate and package from the helper virus); (b) an Epstein-Barr virus (EBV) nuclear antigen (EBNA-1) gene and an EBV latent origin of replication (oriP) which allow the vector to be maintained in episomal form within the nucleus for replication without integration to the host genome and for even replication into each of two dividing cells; preferably (c) genes from prokaryotic cells for propagation of the vector in *E. coli* (a selectable marker gene such as the ampicillin resistance or tetracycline resistance gene and the col. E1 ori) and (d) a sequence encoding a protein which causes the expression of an active α-galactosyl epitope. Optionally the vector may also comprise prokaryotic genes that provide for a second selectable marker such as the genes for positive Hygromycin selection. An example of such virus is PHE700 which is shown in FIG. 5

In this particular embodiment the packaging function of mini-vector DNA into Herpes simplex viral capsids is provided by a helper virus and a helper cell line.

In yet another embodiment the HSV vector can be engineered to produce a helper free viral vector as in Mann et al., "Construction of a Retro-Virus Packaging Mutant and its Use to Produce Helper-Free Defective Retrovirus", 33 Sal., p. 153–159, May 1983, Journal of Virology, September 1989, pp. 3822–3829, September 1989; Samulski "Helper Free Stocks of Recombinant Adeno-Associated Viruses: Normal Integration Does Not Require Viral Gene Expression"; and Kohn et al., "High Efficiency Gene Transfer Into Mammalian Cells: Generation of Helper-Free Recombinant Retrovirus With Broad Mammalian Host Range", PNAS, Vol. 81, pp. 6349–6353, October 1984. See also Okasinki, U.S. Pat. No. 4,970,155 "HSV HELPER VIRUS INDEPENDENT VECTOR", incorporated herein by reference.

In yet another preferred embodiment, the method includes the treatment to reduce the cytotoxicity of viral vectors such as Herpes simplex virus while retaining gene expression, by eliminating the concern of possible recombination during virus propagation and contamination of wild-type viruses in virus stock. According to the embodiment the DNA of a virus is damaged by an agent, for example crosslinking may be introduced to the viral vector causing differential inactivation of viruses, and then photochemical means such as exposure to UV light is used.

In one embodiment a combination of a furocoumarin crosslinking agent such as a psoralen and ultraviolet radiation are used to provide crosslinking and differential inactivation. According to the procedure the photoreaction differentially blocks the processes of DNA or RNA replication and expression, yet the number of viral particles provides for complementation such that all gene products are produced. Thus the method can be used to deliver foreign genes to cells without fear of activation of virus through recombination.

The amount of psoralen and UV exposure can be determined for any system by the methods disclosed herein but briefly involve use of a reporter gene in said vector, the expression of which can be observed. For example disclosed herein is use of the lac-Z reporter gene and observation of gene product by assaying for β-galactosidase activity by staining. Other such reporter gene expression detection systems include alkaline phosphatase, chloramphenicol acetyl transferase, green fluorescent protein, or other proteins expressed and then detected by conjugated antibody systems. The in vitro protocol then involves varying the amount of crosslinking agent and observing gene expression to identify the effective range. This is done in combination with traditional cell staining to identify cell lysis. Contrary to prior thought a balance between inactivation of gene expression and complete virus replication so that the two can be uncoupled by treatment by the method of the invention so that one can be achieved without the other.

In a most preferred embodiment the vector is a Herpes simplex virus type-1 vector which is treated with from about 0.1 to about 1 mg/ml TMP with from about 2 to 8 minutes of UVA irradiation. The best combination with the CgalΔ3 and pHE-lac helper virus was 1 mg/ml TMP with 4 minutes of UVA radiation.

Tumors which may be treated in accordance with the present invention include malignant and non-malignant tumors. Malignant (including primary and metastatic) tumors which may be treated include, but are not limited to, those occurring in the adrenal glands; bladder; bone; breast; cervix; endocrine glands (including thyroid glands, the pituitary gland, and the pancreas); colon; rectum; heart; hematopoietic tissue; kidney; liver; lung; muscle; nervous system; brain; eye; oral cavity; pharynx; larynx; ovaries; penis; prostate; skin (including melanoma); testicles; thymus; and uterus. Examples of such tumors include apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), plasmacytoma, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's experimental, Kaposi's, and mast-cell), neoplasms and for other such cells.

The invention will now be described with respect to the following examples; however, the scope of the present invention is not intended to be limited thereby. All citations to patents and journal articles are hereby expressly incorporated by reference.

EXAMPLES

Example 1

Destruction of Murine Cells by Human Serum and Peritoneal Fluid

The effect of the α1,3 GT gene was studied in peritoneal fluid destruction of murine vector producer cells (VPC). In one such experiment the effect on two peritoneal fluid samples was tested. Sample #1 was from a patient with a benign ovarian cyst and sample #2 was from a patient with colonic adenocarcinoma. Murine VPC were resuspended in peritoneal fluid to resemble the in vivo human situation planned as part of a clinical trial of intraperitoneal (IP) delivery of VPC to treat ovarian cancer. Murine based retroviral VPC LTKOSN.2 VPC (available at Human Gene Therapy Research Institute, Des Moines, Iowa)($2 \times 10^6$ cells) were suspended in 1 ml of 100%, 90%, or 50% peritoneal fluid diluted with R10, seeded into 6 well plates, and incubated for 5 hours at 37° C. All unattached cells were transferred into a new 6-well plate and these unattached cells were counted by trypan blue dye exclusion. Table A notes the number of unattached cells after 5 hours. The population of cells that did not attach by trypan blue exclusion were analyzed as a measure of toxicity induced by the peritoneal fluid (Table A). Cells that attached and survived the exposure maintained high titer ($>1 \times 10^5$ cfu/ml). These results indicated that substantial VPC cytotoxicity occurred after peritoneal fluid exposure.

TABLE A

EFFECT OF HUMAN PERITONEAL FLUID ON VPC

| | Percent Peritoneal Fluid | | |
|---|---|---|---|
| Sample | 100% | 90% | 50% |
| #1 | $1.5 \times 10^6$ cells*<br>25% plating<br>eff. 0% viable | $1.2 \times 10^6$ cells*<br>40% plating eff.<br>0% viable | $0.65 \times 10^6$ cells*<br>68% plating eff.<br>50% viable |
| #2 | $1.7 \times 10^6$ cells*<br>15% plating<br>eff. 0% viable | $1.0 \times 10^6$ cells*<br>50% plating eff.<br>80% viable | $0.3 \times 10^6$ cells*<br>85% plating eff.<br>65% viable |

*Number of Unattached Cells (out of $2 \times 10^6$ cells)

Example 2

Complement Blockade Protects Murine Vector Producer Cells and Retroviral Vectors Another series of experiments were conducted in vitro of Heparin and Lovenox inhibition of complement mediated lysis of murine VPC. Human serum (Lot# 132-06-031396) was applied to cells and viable cells were determined by Trypan blue exclusion. Cells were exposed to serum that had been incubated with various concentrations of heparin or Lovenox as indicated in the Table B.

TABLE B

HEPARIN AND LOVENOX BLOCK VPC LYSIS

| [U/ml] | Heparin (% Viable) | Lovenox (% Viable) |
|---|---|---|
| 25 | 43.6 | 30.5 |
| 12.5 | 14 | 14.8 |
| 6.2 | 4.2 | 8.2 |
| 3.1 | 8.6 | 6.1 |
| 1.6 | 3.7 | 4.7 |
| No Treatment | 1.3 | 1.3 |
| Heat Inactivated | 99.2 | 99.2 |

Example 3

The effectiveness of a specific recombinant protein, sCR1 for inhibition complement mediated lysis of VPC was also tested. sCR1 is a soluble form of complement receptor 1 effectively binds complement and prevents the attach complex. Demonstration of effective blockade of cell lysis by serum with this agent indicates specific function of complement in the lysis event. LTKOSN.2 VPC were exposed to human serum from a stand lot for 30 minutes at 37° C. Cells were then subjected to trypsin digest and counted by trypan blue exclusion to determine viability, results are depicted in Table C.

TABLE C

SCR1 BLOCKS LYSIS OF MURINE VPC

| [sCR1] $\mu$g/ml | Exp. 1 % Viable | Exp. 2 % Viable | Mean % Viable |
|---|---|---|---|
| 50 | 95.9 | 98.7 | 97.3 |
| 25 | 75.1 | 85.2 | 80.2 |
| 12.5 | 38.6 | 41.6 | 40.1 |
| 6.3 | 5.3 | 3 | 4.2 |
| 3.1 | 0.8 | 3.3 | 2.1 |
| 1.6 | 1 | 0.9 | 1.0 |
| 0 | 0.6 | 0 | 0.3 |
| Heat Inact | 98 | 98 | 98.0 |

In the next experiment, the effect of human serum on murine retroviral vectors derived from LTKOSN.2 VPC was determined. In a parallel fashion to the above experiment, a standardized batch of LTKOSN.2 retroviral supernate was harvested (approximate titer $1\times10^6$ cfu/ml). Individual aliquots of vector supernates were exposed to human serum for 30 minutes at 37° C. Individual treatments were done of the replicate samples to test the ability of sCR1, heparin, and Lovenox to prevent inactivation of vector as determined by effect on viral transduction efficiency on tumor cells. Results are depicted in Table D.

TABLE D

RETROVIRAL VECTOR PROTECTION FROM COMPLEMENT INACTIVATION

| Treatment | Conc. of Treatment | Virus Titer CFU/ml | % of Pos. Control |
|---|---|---|---|
| sCR1 | 10 mg/ml | $2.2 \times 10^5$ | 75.9 |
| Heparin | 10 M/ml | $3.7 \times 10^5$ | 127.6 |
| Lovenox | 10 U/ml | $2.0 \times 10^5$ | 67.2 |
| No Treat | none | $1.3 \times 10^5$ | 43.1 |
| Heat Inact | none | $3.9 \times 10^5$ | 132.7 |
| Pos. Control | none | $2.9 \times 10^5$ | 100 |

Example 4

In Vivo Transfer of the $\alpha$1,3 GT Gene to Destroy Tumors

Table E shows the results of a time course experiment illustrating the immediacy of the destruction of murine VPC. According to the invention tumor cell destruction will be induced similar to the immediate cellular and tissue destruction seen with hyperacute rejection after exogenic transplant.

Exposure to human serum for 1 to 4 hours demonstrates that most of the effects of complement destruction occurred very rapidly. Little further murine VPC lysis occurred after the first timepoint. This emphasizes the immediate nature of the antibody to $\alpha$1,3 galactosyl epitopes and rapid complement fixation.

TABLE E

PROTECTION FROM SERUM LYSIS OVER TIME

| Treatment | Conc. | 1 Hr % Viable | 2 Hrs % Viable | 4 Hrs % Viable |
|---|---|---|---|---|
| sCR1 | 30 $\mu$g/ml | 89.6 | 86.7 | 87.8 |
| sCR1 | 20 $\mu$g/ml | 73.7 | 65.9 | 69.9 |
| sCR1 | 10 $\mu$g/ml | 40.2 | 40.8 | 40.7 |
| Heparin | 25 U/ml | 26.9 | 44.9 | 42.7 |
| Heparin | 10 U/ml | 19.1 | 20.7 | 17.1 |
| Lovenox | 25 U/ml | 32.4 | 31.0 | 34.9 |
| Lovenox | 10 U/ml | 12.2 | 13.9 | 15.6 |
| No treat | N/A | 2.3 | 0.0 | 4.0 |
| Heat inact | N/A | 100.00 | 99.3 | 98.2 |

Example 5

Effectiveness of the $\alpha$1,3 GT Gene in inducing Complement Destruction of Human Cells As an initial step several human tumors cell lines were tested for their relative resistance to lysis by human serum. See Table F. As expected, no significant lysis occurred. This same lot of human serum did result in lysis of murine VPC. The A375 human melanoma was chosen for the further analysis since it had previously been used as a model of human melanoma in athymic nude mice.

TABLE F

RESISTANCE OF HUMAN CELLS TO LYSIS BY HUMAN SERUM

| Cell Line | No Treatment % Viable | Heat Inactivated % Viable |
|---|---|---|
| A375 | 97.1 | 100 |
| HTB122 | 85.2 | 83.9 |
| IGROV | 95.9 | 98.6 |
| MCF7 | 77.4 | 76.8 |
| E5 | 98 | 96.9 |

Example 6

The murine version of the $\alpha$1,3 galactosyl transferase enzyme was cloned into the LNCX retroviral vector backbone, Miller, A. D., "Redesign of Retrovirus Packaging Cell Lines to Avoid Recombination Leading to Helper Virus Production", *Molec Cell Biol* (1986) 6:2895–2902. This eukaryotic expression vector was transfected into human A375 tumor cells that were then exposed to human serum.

The next experiment was to test whether or not the A375 clones expressing α1,3 galactosyl epitopes by FACS analysis could be killed by human serum. This initial data demonstrated that the α1,3 galactosyl transferase gene from the mouse can be active in human tumor cells, See Table G.

TABLE G

TESTING A375-A GAL CLONES FOR COMPLEMENT MEDIATED LYSIS

| Cell Line | % Viable |
| --- | --- |
| A375 | 99.3 |
| A375αG.4 | 99.6 |
| A375αG.5 | 96.7 |
| A375αG.6 | 97.0 |
| A375αG.7 | 6.4 |
| A375αG.8 | 38.7 |
| A375αG.9 | 100.0 |
| A375αG.10 | 98.0 |

Example 7

Next the lysis experiment was repeated with two clones that were killed by serum and two clones that were resistant. The results are shown in Table H. Incubation with sCR1 prevented cell killing by serum. The clones demonstrated the same pattern of sensitivity and resistance to serum as the prior trial. In order to test for the direct presence of α1,3 galactosyl epitopes a method previously described by Gallili and colleagues, supra, was used.

TABLE H sCR1 TREATMENT OF A375αG CELLS

| Cell Line | No Treatment % Viable | sCR1 Treated | Heat Inactivated % Viable |
| --- | --- | --- | --- |
| A375 | 98.7 | NC | 96.9 |
| A375αG.7 | 2.6 | 92.0 | 93.9 |
| A375αG.8 | 11.1 | 91.6 | 95.5 |
| A375αG.11 | 96.2 | NC | NC |

Example 8

Human Tumor Cell Clones Susceptible to Serum Killing Express α1,3 Galactosyl Epitopes The ability of certain types of lectins to bind specifically to α1,3 galactosyl epitopes on proteins has been previously determined. In order to demonstrate that the plasmid mediated transfection was inducing effective α1,3 GT gene expression and translation, five hundred $\mu$l of a 1×10$^6$ cell/ml suspension in RPMI 1640 (Gibco BRL, Gaithersberg, Md.) were stained with 10 $\mu$l of a 1 mg/ml solution of Griffonia Simplicifolia isolectin B4 (Vector Laboratories, Burlingame, Calif.). This provided 10 $\mu$g of lectin per sample. The cells and lectin were gently mixed and allowed to incubate at 37° C. for 45 minutes. After incubation the cells were pelleted and resuspended in fresh RPMI 1640 and analyzed by FACS on a EPICS Profile II analyzer (COULTER Laboratories). These results demonstrated selective expression of the α1,3 galactosyl epitope on transfected A375 cells and murine 3T3 cells (positive control), but not on nontransfected A375 cells.

Example 9

The Use of α(1,3)Galactosyl Transferase as an Anti-Tumor Treatment

The next step in preliminary evidence needed to pursue this strategy is to attempt to demonstrate in vivo differences in serum exposed α1,3 GT expressing tumors. This presents a problem in normal murine models since murine cells contain an intact α1,3 GT gene and express α1,3 galactosyl epitopes on their cells. One protocal available is a model development using transgenic knockout mice, commercially available. An experiment in which A375 cells with and without α1,3 GT expression were injected into athymic nude mice after brief (30 minutes) exposure to human serum ex vivo was conducted. In the experiment groups treated with sCR1 were included to demonstrate that complement was responsible for the differences in tumors cells.

As a positive control for tumor killing one group of animals received A375 cells irradiated with 1000 rads. A375-nontransfected tumor cells; Alp Gal-A375 tumor cells transfected with α1,3 GT clone 7; NT-no treatment; sCR1-treatment with 25 mg/ml for 30 minutes; HI-heat inactivated. Five animals were injected subcutaneously with 1×10$^7$ cells each in the various groups. Animals were monitored for tumor growth for up to 28 days. Only animals injected with either irradiated A375 cells (positive control) or A375a7 cells exposed to serum were tumor free. See FIG. 1.

Example 10

Gene Delivery with the phe700 Herpes Simplex Amplicon Vector

Figure 2:
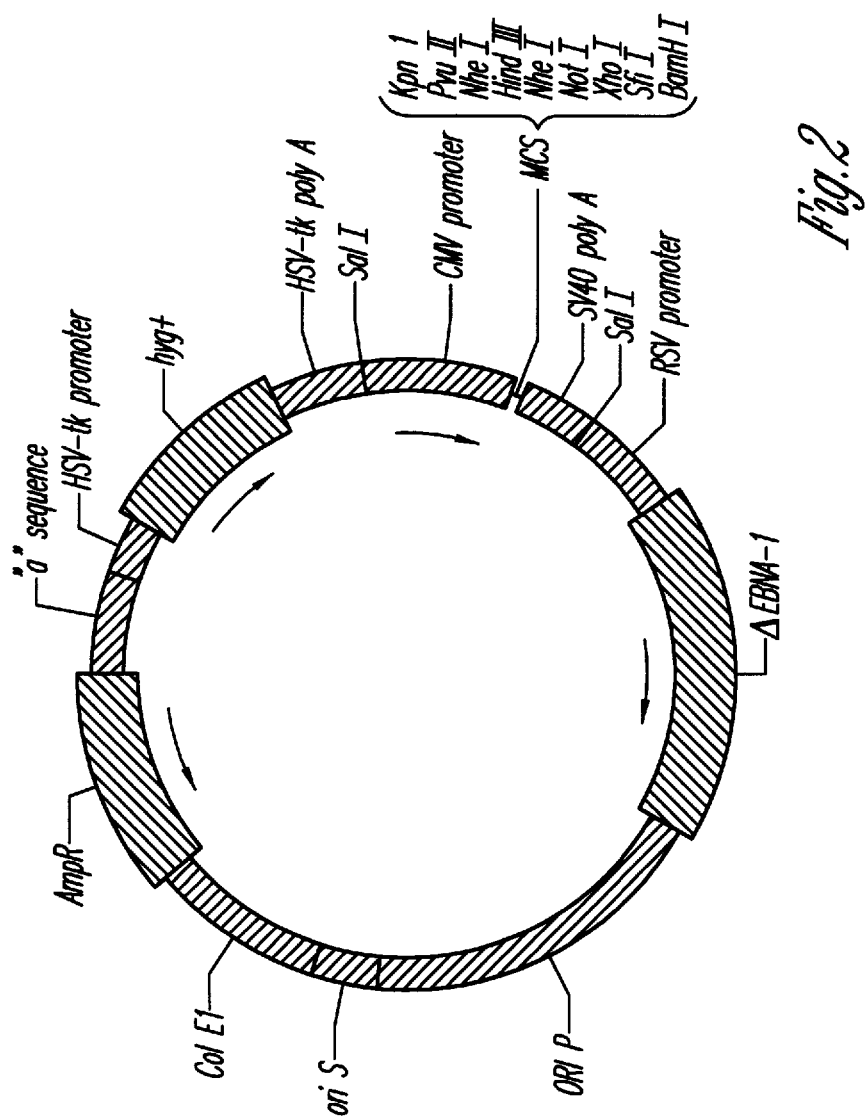
FIG. 2 is a plasmid map of PHE700 vector. Amp$^R$, ampicillin resistant; "a", HSV-1 packaging signal; HSV-tk promoter, HSV-1 thymidine kinase promoter; hyg+, hygromycin resistance; MCS, multi-cloning site; $\Delta$EBNA-1, modified EBV nuclear antigen; ori P, EBV unique latent replication origin; ori S, HSV-1 replication origin.

A novel amplicon vector, pHE, contains HSV-1 ori S and packaging sequences that permits vector replication and packaging into HSV-1 virions. We and another group have constructed a HSV amplicons that also contain Epstein-Barr Virus (EBV) sequences that maintain the plasmid as an episome in the transfected cell nucleus. Westphal, E. M. et al., "A Novel Infectious Mini-HSV for High Efficiency Gene Transfer Into Human Cancer Cells", *Cancer Gene Ther* (1995) 2:324. EBV has been demonstrated to contain a unique latent replication origin (ori P) which directs viral self-replication and maintenance in cells without entering the lytic cycle. Yates, J. L. et al., "Stable Replication of Plasmids Derived from Epstein-Barr Virus in Various Mammalian Cells", *Nature* (1985) 313:812–815; Reisman, D. et al., "A Putative Origin of Replication of Plasmids Derived from Epstein-Barr Virus is Composed of Two Cis-Acting Components", *Mol Cell Biol* (1985) 5:1822–1832. The Epstein-Barr virus nuclear antigen 1 (EBNA-1) encodes a DNA binding transactivator for ori P. Yates, J. L. et al., "Stable Replication of Plasmids Derived from Epstein-Barr Virus in Various Mammalian Cells", *Nature* (1985) 313:812–815; Reisman, D. et al., "A Putative Origin of Replication of Plasmids Derived from Epstein-Barr Virus is Composed of Two Cis-Acting Components", *Mol Cell Biol* (1985) 5:1822–1832; Rawlins, D. R. et al., "Sequence-Specific Interactions of Cellular Nuclear Factir I and Epstein-Barr Virus Nuclear Antigen With Herpes Virus DNAs", *Cancer Cells* (1986) 4:525–542; Goldsmith, K et al., "Identification of EENA1 Amino Acid Sequences Required for the Interaction of the Functional Elements of the Epstein-Barr Virus Latent Origin of DNA Replication", *J Virol* (1993) 67:3418–3426. Investigators previously demonstrated that plasmid vectors containing the EBV ori P that also expressed the EBNA-1 gene were more effective eukaryotic expression vectors. Yates, J. L. et al., "Stable Replication of Plasmids Derived from Epstein-Barr Virus in Various Mammalian Cells", *Nature* (1985) 313:812–815. Various groups have used such EBNA-1 based vectors for expression in human tumors with therapeutic intent. Judde, J. G. et al., "Use of Epstein-Barr Virus Nuclear Antigen-1 in Targeted Therapy of EBV-Associated Neoplasia", *Human Gene Ther* (1996) 7:647–653. The combination of the HSV amplicon with the EBV sequences improves the ease of use of the HSV amplicon system. Our replication incompetent pHE vectors maintained wide tropism for delivering transgene(s) into both dividing and quiescent cells with high efficiency both in vitro and in vivo into the rat brain. Our improved vector could be produced at high titer and could carry and stably package a 21 kb DNA insert. FIG. 2 is a diagram of PHE700 vector.

Episomal Maintenance and Amplicon Vector Packaging.

The maintenance of pHE vector as an episome was demonstrated by transfection of pHE700-lac into E5 cells and selection with Hygromycin. By day 16 of drug selection, almost all cells expressed β-galactosidase. To generate viral stocks, these selected ES cells containing pHE700-lac plasmid were infected with d120 helper virus (kindly provided by N. DeLuca, University of Pittsburgh). The resulting supernatants contain both the pHE700-lac vector and helper virus. The multiplicity of infection (MOI) of the helper virus added was between 0.01 to 0.1 to induce viral vector production within 24–36 hours. The average titer obtained was $2 \times 10^6$ bfu/ml with a ratio of pHE700-lac vector (bfu) to d120 helper virus (pfu) of 1:10.

Transduction and Expression in Vitro of the phe 700-lac Vector

The pHE700-lac containing supernatants were used to transduce human target cells in vitro. The β-galactosidase gene expression was evaluated after infection with pHE700-lac vector (3–10 MOI) in various cultured human cells, including VA13 normal fibroblasts, all cells were fixed and stained with X-gal two days after infection. The expression continued for approximately 2 weeks with a peak expression occurring 48–72 hours after transduction.

Figure 3:
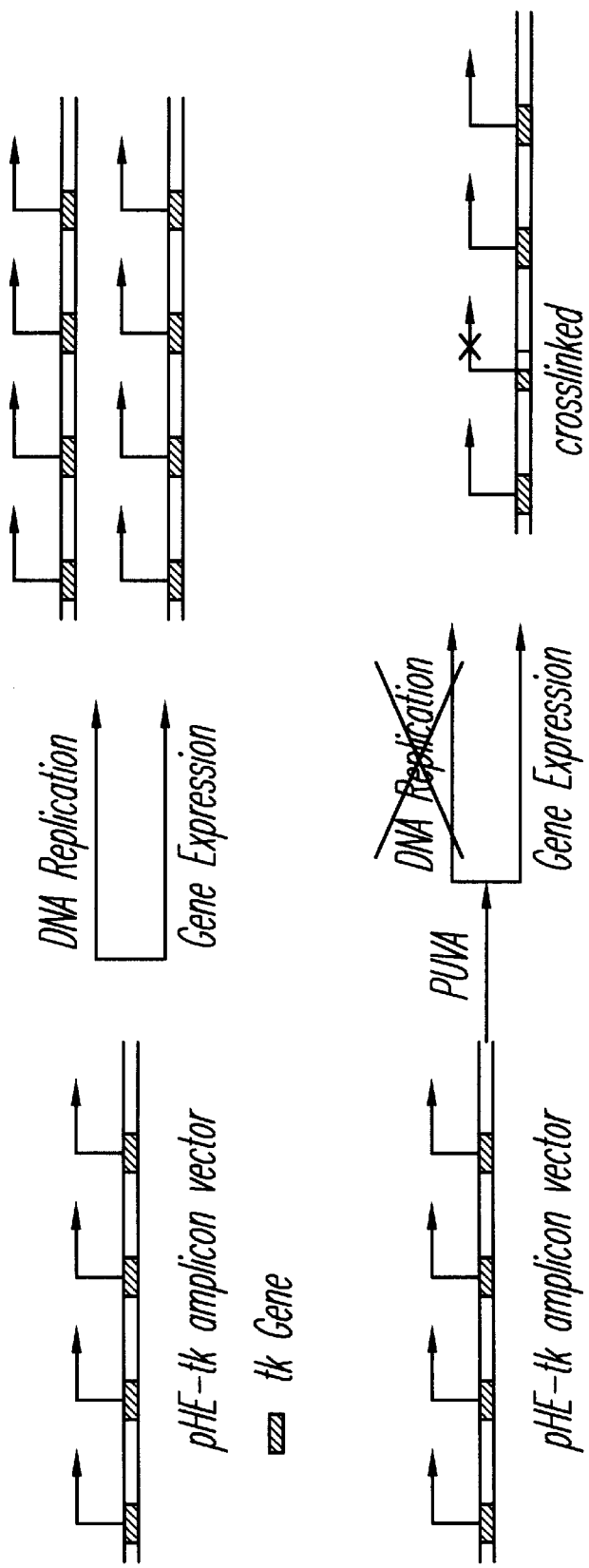
FIG. 3 is a schematic depicting the effects of photochemical modification of PHEtk vector containing tandem repeats of the HSVtk gene expression unit. In permissive cells transduced with unmodified vector, both DNA replication and gene expression occur (top). After PUVA treatment interstrand DNA crosslinks inhibit viral replication, but permit transgene expression from unaffected transcription units.

Hsv Amplicon Vector Cytotoxicity d120 HSV helper virus is necessary to package this HSV amplicon vector. DeLuca, N. A. et al., "Isolation and Characterization of Deletion Mutants of Herpes Simplex Virus Type 1 in the Gene Encoding Immediate-Early Regulatory Protein ICP4", *J Virol* (1985) 56:558–570; DeLuca, N. A. et al., "Activities of Herpes Simplex Virus Type 1 (HSV-1) ICP4 Genes Specifying Nonsense Peptides", *Nucleic Acids Res* (1987) 15:4491–4511. Helper virus d120 has deletions of both IE3 gene loci to prevent viral replication in normal cells, but permits replication in the E5 helper cell line expressing the IE3 gene. DeLuca, N. A. et al., "Isolation and Characterization of Deletion Mutants of Herpes Simplex Virus Type 1 in the Gene Encoding Immediate-Early Regulatory Protein ICP4", *J Virol* (1985) 56:558–570; DeLuca, N. A. et al., "Activities of Herpes Simplex Virus Type 1 (HSV-1) ICP4 Genes Specifying Nonsense Peptides", *Nucleic Acids Res* (1987) 15:4491–4511. This helper virus causes substantial cytotoxicity to infected normal cells in vitro. Unfortunately, there is no method currently available to separate HSV amplicon vectors from helper virus. Our novel method uses psoralen and UVA light (PUVA) to reduce the cytotoxicity of HSV vectors but retain high level gene expression. Psoralens are polycyclic planar molecules that form covalent, cyclobutane-type linkages. Hanson, C. V. et al., "Photochemical Inactivation of DNA and RNA Viruses by Psoralen Derivatives", *J Gen Virol* (1978) 40:345–358. Previous studies applying cross-linking methods with psoralen and UVA completely inactivated virus by blocking DNA replication and viral gene expression to inactive viruses Redfield, D. C. et al., "Psoralen Inactivation of Influenza and Herpes Simplex Viruses of Virus-Infected Cells", *Infect Immun* (1981) 32:1216–1226; Swanstrom, R et al., "Interaction of Psoralen Derivatives With the RNA Genome of Rous Sarcoma Virus", *Virology* (1981) 113:613–622; Alter, H. J. et al., "Photochemical Decontamination of Blood Components Containing Hepatitis B and Non-A, Non-B Virus", *Lancet* (1988) 2:1446–1450; Hanson, C. V., "Photochemical Inactivation of Viruses With Psoralens: An Overview", *Blood Cells* (1992) 18:7–25; Lin L. et al., "Photochemical Inactivation of Cell-Associated Human Immunodeficiency Virus in Platelet Concentrates", *Blood* (1993) 82:292–297; Cotten, M. et al., "Psoralen Treatment of Adenovirus Particles Eliminates Virus Replication and Transcription While Maintaining the Endosomolytic Activity of the Virus Capsid", *Virology* (1994) 205:254–261. In our experiments, the appropriate PUVA dose induces DNA crosslinks in the vector that result in differential inactivation of viral replication and transgene expression. See FIG. 3. Treatment of a Herpes simplex virus type 1 vector with 0.1 to 1 mg/ml TMP with from 2 to 8 minutes UVA radiation successfully inhibited replication while retaining expression. PUVA exposure inhibited viral replication in the E5 helper cell while retaining gene expression of a reporter gene product.

Example 11

Ex Vivo Protocols for Purging of Cells. A Doxycycline Inducible Retroviral Expression Vector that Can Selectively Cause Complement Mediated Destruction of Lymphocytes Exposed to Human Serum Adoptive transfer of lymphocytes modified to treat graft versus host disease (GvHD) after allogeneic bone marrow transplantation.

Allogeneic BMT (bone marrow transplant) cures leukemia by means of myeloablation induced by the preparative regimen and by transfer in the bone marrow allograft of immunocompetent donor cells that exert an anti-leukemic effect called Graft-versus-Leukemia (GvL). Horowitz MM et al. "Graft-Versus-Leukemia Reaction After Bone Marrow Transplantation", *Blood* 1990; 75:555–562; Weiden, P. L., Horowitz M. M., "Graft-vs-Leukemia Effects in Clinical Bone Marrow Transplant", *Hematology* 1990; 12:691–708. Recently direct evidence for this anti-leukemic effect was demonstrated by the infusion of donor peripheral blood leukocytes into patients with relapse after allogeneic BMT (Table I). The International Bone Marrow Transplant Registry analyzed data from 2,254 patients who underwent HLA-identical sibling BMT for early leukemia and found a significant reduction in the relapse risk for patients who developed GvHD. Horowitz M. M. et al. "Graft-Versus-Leukemia Reaction After Bone Marrow Transplantation", *Blood* 1990; 75:555–562; Weiden, P. L., Horowitz M. M., "Graft-vs-Leukemia Effects in Clinical Bone Marrow Transplant", *Hematology* 1990; 12:691–708. Sadly, GVHD is not always treatable and causes substantial patient morbidity and mortality. The removal of mature T-cells from the graft results in effective prevention of acute and chronic GvHD. This benefit of T-cell depletion is offset by increased graft failure and leukemia relapse so that overall survival is not improved. Marmont, A. M. et al., "T-Cell Depletion of HLA-Identical Transplants in Leukemia", *Blood*, 1991; 78:2120–2130. T-cell depletion increases leukemia relapse in AML and ALL because of the loss of GvHD. In the case of cell CML there is also a GvL effect (independent of GvHD) which may be lost during the process of T-cell depletion. Kolb and colleagues first reported that for patients who relapse with CML after allogeneic BMT, leukocyte infusions from the original donor can induce remission. Kolb, H. J. et al., "Donor Leukocyte Transfusion for Treatment of Recurrent Chronic Myelogenous Leukemia in Marrow Transplant Recipients", *Blood,* 1990; 76:2462–2465. Existing data finds that patients with CML who have cytogenetic relapse only or chronic phase respond better to this treatment than patients with more advanced disease. In conclusion, allogeneic BMT is associated with a GvL effect that has a GvHD-dependent and a GvHD-independent component. Current drug therapy for GvHD is only partially effective and progressive GvHD destruction of recipient tissues is often fatal. Therefore, it is highly desirable to be able to destroy adoptively transferred lymphocytes only if they cause GvHD.

TABLE I

Donor Leukocyte for Relapse after ABMT

| Disease | Cells ($10^8$/kg) | Other Rx | ↓WBC | GvHD | Resp. | Ref |
|---|---|---|---|---|---|---|
| 3 CML | 4.4–7.4 | IFNα | NR | 2/3 | 3/3 | 7 |
| 4 AML | 3.3–9.1 | Ara-C, Amsa | NR | 3/4 | 1/4 | 8 |
| 6 CML | 0.3–3.4 | IFNα, Busulf | 2/6 | 5/6 | 4/6 | 9 |
| 8 CML | 2.5–5.0 | IFNα | 4/8 | 7/8 | 6/8 | 10 |
| 51 CML | NR | IFNα | NR | NR | 36/51 | 11 |
| 23 AL | | | | | 8/23 | |
| 11 CML | 0.9–8.4 | IFNα | 5/11 | 9/11 | 6/11 | 12 |
| 14 CML | 0.6–10.1 | IFNα, Hydrea | 2/14 | 9/14 | 10/14 | 13 |
| 6 CML | 1.1–16.4 | IFNα | NR | NR | 3/6 | 14 |
| 13 AL | | | | | 3/13 | |
| 84 CML | 0.1–15.0 | IFNα | 28 | 55 | 54/84 | 15 |
| 45 AL | | | 13 | 21 | 5/45 | |

NR-not reported; AL-acute leukemia

Retroviral Transduction of Rodent and Human Lymphocytes

Figure 4:
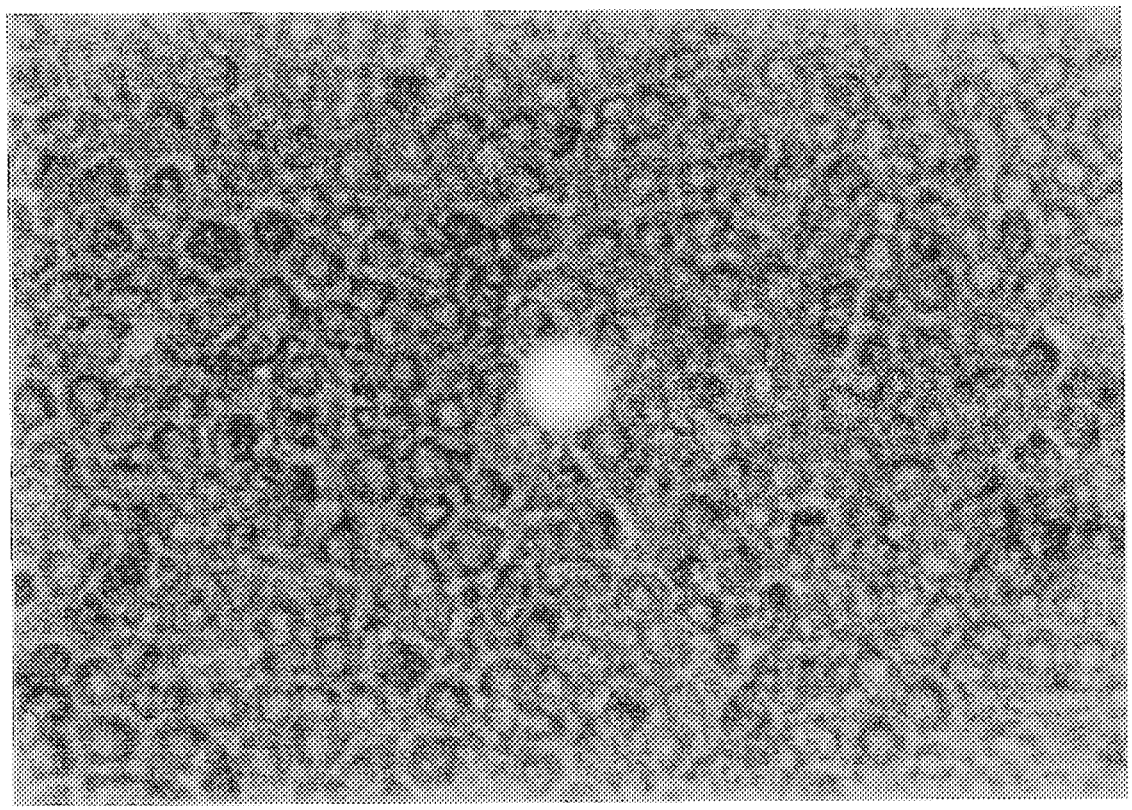
FIG. 4 is a photograph depicting lymphocytes transduced by murine LNChRG retroviral vector expressing a humanized, red shifted GFP mutant gene. Lymphocytes were transduced by phosphate depletion method. The living cells were visualized with an FITC filter at 100× magnification

Efficient retroviral transduction of lymphocytes is the first requirement for an ex vivo approach using the α((1,3)GT gene to ablate GvHD inducing T-cells. Our laboratory has previously developed a protocol for adoptive immunotherapy using retroviral gene transfer of the HStk gene. The problems with the HStk gene transfer approach are two fold. First, the transduced lymphocytes require drug selection after transduction with neomycin to eliminate non-transduced cells and the selection can damage T-cells (data not shown). The second problem is that some patients who have completed an allogeneic bone marrow transplant develop significant infections with Cytomegalovirus (CMV) or HSV that requires treatment with GCV or acyclovir. If such infections occur, the anti-viral therapy would destroy the adoptively transferred gene modified lymphocytes. Since recurrent leukemia patients (especially CML patients) have a substantial response rate to adopted lymphocytes that may be curative, premature destruction of donor lymphocytes in the absence of substantial or refractory GvHD may be harmful to the patient. For this project we propose solutions to these two concerns. To permit lymphocyte sorting without drug selection, our vector will contain a humanized, red-shifted green fluorescent protein (hRGFP) gene (See FIG. 4). The second major modification is the use of doxycycline inducible promoter (dip) for control of the α(1,3)GT gene expression. The dip regulatory cassette will be incorporated into a retroviral vector. We previously demonstrated the results of FACS sorting of hRGFP expressing tumor cells. Approximately a 3 log increase in mean green fluorescent intensity was noted with expression from the retroviral construct. This shift will make it straight forward to sort GFP gene modified lymphocytes as well. We have also previously transduced human lymphocytes with the HStk gene and demonstrated that they can be inhibited by GCV. Under optimal conditions, greater than 90% of the HStk transduced and selected lymphocytes can be destroyed.

Gene Modified Lymphocytes Remain Alloreactive

The alloreactivity of peripheral blood lymphocytes with and without transduction with the LTKOSN.2, commercially available at HGTRI, Des Moines, Iowa, vector was determined. The assay used the incorporation of [$^3$H]-thymidine to determine proliferation rates after stimulation with irradiated LCL/HA lymphoblastoid cells or irradiated, pooled human peripheral blood mononuclear cells. Three days after stimulation with allogeneic cells the rate of [$^3$H]-thymidine incorporation increased substantially for all three cell lines (Table J). These results demonstrate that transduced peripheral blood lymphocytes remain alloreactive compared to non-transduced control cells. The phenotype of the transduced lymphocyte population did not change significantly either. The percentage of CD8+ (53–79%) and CD4+ (20–44%) T-cells in retroviral transduced cells did not vary from nontransduced control cells.

TABLE J

ALLOREACTIVITY OF TRANSDUCED HUMAN LYMPHOCYTES

| Cell Line | +LCL HA.NV (cpm) | −LCL HA.NV (cpm) | +POOLED PBM* (cpm) | −POOLED PBM (cpm) |
|---|---|---|---|---|
| PBL.NV | 8,280 | 145.0 | 12,920 | 76.0 |
| PBL-1.TK | 9,100 | 425.0 | 14,100 | 362.0 |
| PBL-2.TK | 6,355 | 248.0 | 10,710 | 113.0 |

*PBM—Human Peripheral Blood Mononuclear Cells

Example 12

The α(1,3)GT gene was cloned into the pREP7 vector (Invitrogen) and then into the multi-cloning site of LXSN retroviral vector backbone (kindly provided by A. D. Miller, University of Washington) to generate the LαGTSN vector. LXSN contains modifications to minimize breakouts of replication competent retrovirus. Miller, A. D., et al., "Redesign of Retrovirus Packaging Cell Lines to Avoid Recombination Leading to Helper Virus Production", *Molec Cell Biol.,* 1986; 6:2895–2902. The vector has been thoroughly described elsewhere and has previously been used for in vitro transfer and killing of breast cancer and ovarian cancer cells using the HStk gene and GCV system (see Appendix: Reprint 4 & 7). Link, C. J., Kolb, E., Muldoon, R., "Preliminary In Vitro Efficacy and Toxicities Studies of the Herpes Simplex Thymidine Kinase Gene System for the Treatment of Breast Cancer", *Hybridoma,* 1995; 14:143–147; Link, C. J., et al., "A Phase I Trial of In Vivo Gene Therapy with the Herpes Simplex Thymidine Kinase/ Ganciclovir System for the Treatment of Refractory or Recurrent Ovarian Cancer", *Human Gene Ther,* 1996; 7:In press. The LAGTSN vector efficiently transfers a sensitivity to human serum into human A375 melanoma cells. This sensitivity is complement mediated and correlates with α(1,3)galactosyl epitopes on the cell's surface.

Recombinant α(1.3)GT Protein Production and Western Analysis

Our initial results indicate that lectin can specifically bind the α(1,3)galactosyl epitope and allow analysis by FACS. To find how the level of α((1,3)GT enzyme production relates to the amount of detected α(1,3)galactosyl linkages, western analysis will be performed of α(1,3)GT transduced human tumor cells and lymphocytes. A polyclonal anti-α((1,3)GT antibody for the protein will be produced as follows. An α1,3)GT prokaryotic expression vector (pT7, Margaret Black, University of Washington) in which the α(1,3)GT gene is controlled by the T7 promoter will be transfected into competent BL21 DE3 pLYS-S *E. Coli* (Novagen) and selected on Ampicillin LB plates. Single colonies will then be grown in NZCYM media. IPTG (1 mM) will next be added for 3 hours. Induction of α(1,3)GT protein will be confirmed by PAGE/Coomassie and western analysis with the anti-α(1,3)GT antibody. The bacterial recombinant α(1,3)GT protein will be isolated from a PAGE gel, electroeluted, dialyzed and lyophilized. This protein will be used to immunize rabbits (per protocol from Animal Pharm Services). Western Analysis: PA317 cells (20,000) will be transiently lipofected (DOTAP, Boheringer Mannhiem) with 1 μg of pLαGTSN plasmid in DMEM w/o serum for 6 hours. DMEM w 10% FCS will then be added and 36 hours later cells are harvested with loading buffer (1 ml) and boiled for 2 minutes. PA317 cells (not transfected) and LαGTSN VPC will be harvested as negative and positive controls respectively. Lysates will be loaded onto a 10% denaturing PAGE gel and run at 9 W for 2 hours (Hoefer, Mighty Small) with kaleidoscope standards (BioRad) and recombinant LαGTSN protein as an antigen marker. The gel will be electroblotted (BioRad Transblot) onto nitrocellulose paper (Sigma, 0.45 μm, N-9888). The blotted nitrocellulose will be blocked with TBST/1% carnation dry milk for 1 hour. The rabbit polyclonal anti-α(1,3)GT antibody will be added at the appropriate dilution depending on effective concentration to detect purified α(1,3)GT protein for 2 hours in TBST. Following TBST washes an anti-rabbit IgG peroxidase conjugated antibody (Sigma, A9169) will be added to the blot at 1:50,000 dilution. After additional TBST washes the blot will be developed with a chemiluminescent reagent (ECL, Boeringer Mannhiem) and exposed to XAR film.

Human lymphocytes (2×107) will be transduced by the phosphate depletion described in the Preliminary Data section. LαGTSN transduced lymphocytes will then be studied by western analysis for α(1,3)GT protein production. For western analysis 20–50×105 cells will be lysed and analyzed as described above. Nontransduced lymphocytes will serve as negative controls and A375αG.7 cells (transduced with LαGTSN vector) will serve as positive controls. These LαGTSN transduced lymphocytes will next be evaluated by FACS as previously described in the preliminary data section. Lymphocytes will be analyzed either 72 hours after transduction or after 5 days of selection in G418 (500 μg/ml). Data will be reported as percent α(1,3)GT positive in FACS zones corresponding to the presence of α(1,3)GT epitopes selectively exposed to a standardized human serum with active complement levels.

Subcloning to Obtain High Titer LαGTSN VPC Clones

During his period, another set of LαGTSN VPC will be constructed by transducing fresh PA317 fibroblasts with filtered vector supernates from the transfected selected cells. These additional steps will be taken because our experience has been that transduced and selected individual VPC clones generate consistently the highest retroviral titers (5–10×10$^7$ cfu/ml). The plasmid pLαGTSN will be transiently lipofected (lipofectin, Gibco BRL) into the ecotropic packaging cell line GP+E86 (kindly provided by Arthur Bank) and supernates used to transduce PA317 cells. The transduced PA317 line will then be selected in G418 (1 mg/ml) for two weeks. Surviving cells will be subcloned by limiting dilution. Supernates will be collected from 20 independent, subcloned LαGTSN VPC when they grow to 90–100% confluence. Supernates will be filtered through 0.22 μm filters (Nalgene), supplemented with 2 μm/ml of protamine sulfate (Elkins-Sinn) and transferred into tissue culture flasks containing IGROV tumor cells to determine titer (cfu/ml). Twenty-four hours after retroviral transduction the cells will be selected in G418 for 2 weeks. Target cell colonies containing greater than 50 cells will be scored and the vector titer calculated. These higher titer LαGTSN VPC will be used as the source of supernates for lymphocyte transductions in order to maximize gene transfer.

Example 13

Effective GFP Sorting of Transduced Murine and Human Lymphocytes to Recover Vector Transduced T-Cells Without Drug Selection To evaluate the gene transfer efficiency in vivo using the RV or HSV transfer vectors expressing the green fluorescent protein (GFP) and α(1,3)GT genes. A key part of evaluating and developing any gene therapy strategy is to accurately measure gene transfer efficiency. This data is essential in order to make predictions about the amount of vector transduction required to obtain a therapeutic level of the transgene in vivo. The two steps of this process are to obtain a standardized stock of vector supernates and then to measure transgene activity. Gene transfer can be evaluated by using marker genes to easily visualize gene transfer and expression. We will employ a variant GFP gene. This novel marker protein does not require any special staining or fixation procedures. Single copy gene expression is visualized after RV transfer within 24 hours after supernate exposure.

Fluorescent Detection of Green Fluorescent Protein Expressing Lymphocytes

The hGFP-S65T expressing lymphocytes will be visualized with a Nikon Labophot-2 fluorescent microscope (Fryer Company, Inc.). The filter cube used in the microscope was the FITC dichromic filter set (excitation at 450–490 nm and emission at 520 nm). Cell spins will be spread on coverslips, inverted and placed on a glass slide for viewing. Photographs will be taken using a Nikon Microflex AFX-DX systems( Fryer Company, Inc.). Selected high power fields will be photographed with and without background lighting to allow manual calculation of GFP positive cells relative to nonfluorescent cells.

Fluorescence Activated Cell Sorter Analysis of LNCHG65T Transduced Lymphocytes Cytometry of transduced cells will be performed on a Epics Profile II analyzer (Coulter Corp.) with an excitation light of 488 nm. Cells were analyzed using a 525 nm band pass filter set (Part #814036, Coulter Corp.). Cultures of nontransduced lymphocytes, as well as LNChG65T vector transduced lymphocytes will be washed with RPMI with 10% FCS and resuspended at a concentration of approximately $1 \times 10^6$ cells/ml. Tumor cells will be harvested at 80–90% confluence, trypsin digested, and washed and suspended at the same concentration as the lymphocytes. All FACS analysis will use the FL1 emission channel to monitor green fluorescence (normally a FITC monitor).

Lymphocytes will be transduced using the phosphate depletion protocol referenced in the preliminary data section in order to increase yield. For FACS analysis $2 \times 10^6$ cells will be sorted and cells demonstrating a minimum 2 log shift in detected (525 nm) green fluorescence will be obtained. If the rhGFP gene vector does not provide sufficient selection than an alternate version of the gene developed by Brain Seeds and colleagues will be employed. Lymphocytes will be tested by trypan blue exclusion to determine their viability after flow cytometry. The ratio of expected to obtained GFP positive lymphocytes will be calculated by comparing the FACS analysis data (number of cells with 2 log shift in mean fluorescence) to the number of viable GFP positive cells after sorting. This ratio can be used to determine the total number of lymphocytes that would be needed initially to obtain a FACS selected, transduced population of cells.

EXAMPLE 14

Recovery and Detection of GFP Positive Murine Lymphocytes from Mice Infused with Ex Vivo Gene Modified, Facs Selected Cells and Determined the Optimal Duration of GFP Lymphocyte Survival Fluorescent cells will be detected as described above. Mice will undergo serial blood draws after being infused with retroviral vector modified cells. Table K provides an experimental scheme to follow the mice. Six to 8 weeks old, female C57B1/6 mice (approx. 50 gm) will be used for a syngeneic lymphocyte transfer procedure. Lymphocytes will be transduced by the optimized transduction procedure discussed above. Lymphocytes separated from peripheral blood aliquots will be transduced with either LZSN retroviral vector (contains the LacZ gene) or NChRG retroviral vector. Forty-eight hours after transduction cells aliquots will be FACS sorted to analyze the percentage of GFP positive cells. Cell numbers to be injected will be adjusted to obtain the number of gene modified lymphocytes noted in Table 12. Lymphocytes will be injected via the lateral tail vein in 100–1000 μl of HBSS. Two animals from each group will be sacrificed at 5 day intervals. At the time of sacrifice the animals will be anesthetized and subjected to cardiac puncture. Blood samples will be diluted in HBSS and analyzed by FACS and fluorescence microscopy. The percentage of lymphocytes demonstrating green fluorescence will be quantitated by both methods.

TABLE K

DETECTION OF GFP TRANSFER

| Group | Vector | Lymphocytes (cells/kg) | Number of mice |
| --- | --- | --- | --- |
| A | LTKSN | $5 \times 10^8$ | 10 |
| B | LNCrhG | $1 \times 10^7$ | 10 |
| C | LNCrhG | $5 \times 10^7$ | 10 |
| D | LNCrhG | $1 \times 10^8$ | 10 |
| E | LNCrhG | $5 \times 10^8$ | 10 |

The experiment will be repeated at least once. This is necessary to determine whether or not individual lymphocyte preparations have variable survival or transgene expression. If lymphocytes are still expressing GFP as determined by FACS or microscopy on day 25 (the final time point) then the next experiment will be conducted with blood draws performed at 10 day intervals. If some dosages of lymphocytes do not permit detection on serial blood sample analysis, then these doses will be deleted from later experiments.

Example 15

A Retroviral Vector Containing the α(1,3) GT Gene Controlled by the Doxycycline Inducible Promoter (dip)

Generation of Final Retroviral Vector Containing the α(1,3)GT Gene Under Control of the Doxycycline Inducible Promoter and also Containing the GFP Gene.

The second series of vectors that will be cloned will not contain G418 drug selectable markers (neor). Instead, these vectors will contain variants of the green fluorescent protein (GFP). We will employ for our initial studies a recently developed codon optimized, red shifted mutant GFP gene used in the above experiments. Since this marker allows the detection in vitro and in vivo of gene transfer without the need for fixation, α(1,3)GT transduced lymphocytes can be selected by FACS or observed directly in frozen tissues sections. The retroviral plasmid pLdiαCG will be cloned by inserting the α(1,3)GT gene under control of the doxycycline inducible promoter (diP). See FIG. 5.

The diP expression cassette (kindly provided by Dr. Reeves, Mass. Gen Hospital) contains a mutated tetracycline repressor (mtetR) expressed from CMV immediate early promoter. The modified tetR gene contains amino acid substitutions that result in binding of doxycycline (DCN) and then activation of the tetracycline responsive element (TRE) promoter region. The TRE element is fused to a truncated CMV promoter. Binding to the TRE element by the doxycycline and mtetR protein complex results in the induction of high level gene expression. The α(1,3) GT gene will be cloned just downstream of this promoter. The final vector once integrated and expressed in target lymphocytes should exhibit induced expression of α(1,3)GT protein and subsequent presentation of α(1,3)galactosyl epitopes on the cell surface. The α(1,3)GT gene will be PCR amplified from the pLαSN vector to include Sac II and XbaI restriction sites at the 5' and 3' end of the gene's open reading frame respectively. This PCR product will be restriction digested with Sac II and Xba I and cloned into the Sac II and XbaI site of plasmid pTRE (Clontech Corp., Palo Alto, Calif.) to obtain plasmid pTREα. Plasmid pTet-on containing the mtetR and VP16 fusion gene under control of the CMV promoter will be PCR amplified from the plasmid to contain flanking Xba I sites and then cloned into the corresponding site of plasmid pTREα. Restriction analysis and sequencing will be done to obtain intact mtetR gene inserts in both the 5' to 3' and 3' to 5' orientation to obtain pTαdi5 and pTαdi3 respectively. The doxycycline inducible cassette will next be cloned into plasmid pLhRGSN (provided by R. Muldoon, HGTRI, IA). This plasmid contains the same red shifted, humanized hRGFP gene in the LXSN retroviral backbone. The α(1,3)GT expression cassettes from both the pTαdi5 and pTαdi3 plasmid will be cloned downstream of the hRGFP gene at the available Xba I site and blunt end ligated to the 3' LTR sequence. The resulting plasmids pLGTαdi5 and pLGTαdi3 will have constitutive GFP expression from the Maloney virus LTR and doxycycline inducible expression of α(1,3)GT.

Generation of LGTαdi5 and LGTαdi3 Vector Producer Cells

The plasmid pLGTαdi5 and pLGTαdi3 will be transfected into the amphotropic packaging cell line PA317 (kindly provided by A. D. Miller) and selected in G418 (400 μg/ml) for 2 weeks. Supernates will be removed after transient transfection before being placed under G418 selection. These transient supernates will be filtered through 0.22 μm filters (Nalgene), supplemented with 2 μg/ml of protamine sulfate (Elkins-Sinn) and transferred onto new PA317 cells. After 24 hours these transduced cells will be placed under selection. This step is done to attempt to obtain transduced PA317 clones as quickly as possible; however, the results are variable since the viral titers that might be obtained from these plasmid constructs is undefined. Therefore in parallel, the G418 selected and transfected PA317 cells will be grown to 80–90% confluence (after being removed from G418 selection) and also used as a source of supernates to transduce PA317 cells.

Supernates will be collected from cultures of LGTαdi5 and LGTαdi3 VPC when cells reach 90–100% confluence. Supernates will be filtered, protamine added and frozen at −70° C. in standard 50 ml aliquots. Target tumor cells will be transduced by twice daily applications of vector supernates with protamine for 3 days. Lymphocytes will be transduced using the phosphate depletion protocol (as discussed previously). Twenty-four hours after the final exposure to retroviral supernates the transduced cells will be selected, analyzed and sorted by FACS for GFP expression. These surviving α(1,3)GT transduced cells will then be pooled for In vitro experiments. In general the titer of a mixed population VPC is not as high as some isolated individual VPC clones. The bulk VPC population will permit functional and efficacy experiments to be initiated, but it is highly desirable to obtain individual, higher titer clones. These VPC clones are also required by the FDA in human trials. Therefore, individual clones will also be screened.

Screening for Replication Incompetent, High Titer LGTαdi5 and LGTαdi3 VPC Clones Bulk, mixed population of LGTαdi5 and LGTαdi3 VPC will be cloned by limiting dilution into 96-well plates. Twenty individual VPC clones derived from transduced PA317 will be screened for titer. Titer will be determined by screening and counting fluorescent cells 48 hours after a single transduction of A375 melanoma cells plated in 6-well plates. Titer will be expressed as green forming units (gfu/ml). The 3 highest titer lines for each vector (LGTαdi5 and LGTαdi3) will be tested further for stability by serial passage and Southern analysis and clone growth rate. High titer clones will be tested by Southern analysis to insure only a single retroviral integration is present. The optimal clone based on titer, stability, and growth rate will be completely characterized for DCN inducible expression of α(1,3)GT and by FACS. Larger scale culture of these clones will be done to generate 2 to 3 liters of uniform, high titer supernate. This standardized supernate will be used for further in vitro and in vivo tests of the adoptive immunotherapy strategy.

Effective Induction of α(1.3)GT with DCN in a Population of FACS sorted human A375 Tumor Cells Since tumor cells are easier and less expensive to grow and manipulate, initial characterization of vector function and activity will be done using the A375 human melanoma cell line. Previously we have used the A375 tumor cells to study transduction and FACS sorting with hRGFP gene. Levy, J. P., "Retroviral Transfer and Expression of Humanized, Red Shifted Green Fluorescent Protein Into Human Tumor Cells", *Nature Biotechnol*, 1996;14:610–614. This cell line demonstrates uniform intense green fluorescence after single copy transduction with the GFP gene. Therefore, A375 cells will be used for initial study of combining GFP mediated FACS sorting and α(1,3)GT induction with DCN. A375 cells will be transduced with high titer LGTαdi vector supernates by twice daily exposure for 3 days. One day after the final transduction cells will be cloned by limiting dilution into 96-well plates. Five LGTαdi transduced A375 clones (A375αdi.1–A375αdi.5) that demonstrate excellent fluorescence by microscopy will be fully characterized. Each of the 5 clones will be plated into one well of each of five replicate 6-well plates. Cells from one plate will be harvested by standard trypsin digestion on days 0, 2, 4, 7 and 10 after adding DCN (Table L). Negative control will also be harvested on the same days for comparison. Two million cells will undergo flow cytometry to evaluate the presence of α(1,3)galactosyl epitopes by lectin binding. Other cells from these samples (2×104) will be boiled and protein extracted for western analysis. At this stage the relative efficacy of the two retroviral constructs can be most effectively compared. The expression cassette (5'–3' or 3'–5') that demonstrates the best DCN induction will be used for in vivo lymphocyte experiments and in vivo adoptive therapy experiments in transgenic mice.

TABLE L

INDUCTION OF α(1,3) GALACTOSYL EPITOPES BY DCN

| Clone | DCN (μg/ml) | |
|---|---|---|
| A375 No vector | 0 | 2.0 |
| A375αdi.1 | 0 | 2.0 |
| A375αdi.2 | 0 | 2.0 |
| A375αdi.3 | 0 | 2.0 |
| A375αdi.4 | 0 | 2.0 |
| A375αdi.5 | 0 | 2.0 |

The A375 clones will next be tested for complement mediated destruction by human serum. Individual clones and a nontransduced A375 (no vector) clone will be exposed to human serum processed in several ways (Table M). After 30 minutes exposure at 37° C, cells will be evaluated for viability by trypan blue exclusion. These data should allow an exploration of the vector in human lymphocytes.

TABLE M

Human Serum Effect on A375αdi Cells

| | Human Serum Exposure (37° C. for 30 min) | | | |
|---|---|---|---|---|
| Cell Line | No Treatment | sCR1 (μg/ml) | Lovenox (μg/ml) | Heat Inactivated |
| A375 No vector | — | 25 | 25 | yes |
| A375αdi.1 | — | 25 | 25 | yes |
| A375αdi.2 | — | 25 | 25 | yes |
| A375αdi.3 | — | 25 | 25 | yes |
| A375αdi.4 | — | 25 | 25 | yes |
| A375αdi.5 | — | 25 | 25 | yes |

Complement Mediated Destruction of FACS Sorted, Retroviral Transduced Human Lymphocytes and Induce Serum Sensitivity with Doxycycline After completion of analysis of the LtiαSG vector with A375 tumor cells, the efficacy of the vector to function in transduced human lymphocytes will be tested. To optimize for use in lymphocytes, the GFP containing vector will be employed. Under conditions of optimized lymphocyte transduction, the LGTαdi vector system will be evaluated in populations of human lymphocytes. Cells will be propagated in the presence of various concentrations of DCN for various periods of time. This study will be conducted in an analogous manner to the approach with the A375 clones described above. Briefly, 48 hours after transduction human lymphocytes will be subjected to FACS sorting for a two log shift in mean green fluorescence (detection 525 nm). The sorted, GFP positive lymphocyte population will then be split into aliquots for further testing. Cells will be exposed to DCN (0,2.0 or 4.0 μg/ml) for 0, 2, 4, 7 and 10 days. Cells will be analyzed by FACS for α(1,3)galactosyl epitopes by lectin binding. These data should establish the optimal concentration and duration of DCN to activate α(1,3)GT expression from the LGTαdi vector. This information will be used as the starting point for in viva conditions in the α(1,3)GT gene knockout mouse.

Example 16

Ex Vivo Transduction of Murine Lymphocytes Derived from the α(1,3)GT Knockout Mouse Ex vivo Transduction and Analysis of T-Cells Derived From α(1,3)GT Knockout Mice.

Adoptive immunotherapy will be evaluated in the α(1,3) GT knockout mouse model by conducting syngeneic adoptive lymphocyte transfers. Lymphocytes obtained from α(1,3)GT knockout mice will be cultured in RPMI with 10% FBS at 37° C. in 5% $CO_2$ as described for other rodent cells (see Preliminary Data). Lymphocytes will be transduced with the LGTαdi vector system. Cells will be propagated in the presence of various concentrations of doxycycline for various periods of time. This study will be conducted in an analogous manner to the approach with the A375 clones described above. Briefly, 48 hours after transduction lymphocytes will be subjected to FACS sorting for a two log shift in mean green fluorescence. GFP positive lymphocyte population will then be split into aliquots for further testing. Cells will be exposed to DCN (0, 2.0 or 4.0 μg/ml) for 0., 2, 4, 7 and 10 days. Cells will then be analyzed by FACS for α(1,3)galactosyl epitopes by lectin binding. These data should establish the optimal concentration and duration of DCN to activate α(1,3)GT expression from the LGTαdi vector. This information will be used for in viva conditions in the α(1,3)GT gene knockout mouse.

Induction of α(1.3)GT Gene Expression by the Administration of Doxycycline to Mice Infused with Retroviral Vector Modified Lymphocytes Briefly, mice will be kept in standard rat cages and fed food and $H_2O$ ad libitum. Donor mice will be sacrificed after anesthesia and cardiac puncture to obtain whole blood and single cell suspensions will be prepared from in pooled culture media. LGTαdi transduced lymphocytes will be harvested and injected into the lateral tail vein of 6–8 week old female mice housed in microisolator cages with filter tops, and fed sterile food pellets and water ad libitum. The dose of lymphocytes will be derived from the results of the GFP persistence experiment above, but will not be greater than 2.5×108 cells/kg. The murine in vitro experiments will subsequently be done with lymphocytes from donor BALB/c mice (positive controls), nontransduced α(1,3)GT knockout mouse lymphocytes, and LtiαSG vector transduced α(1,3)GT knockout mouse lymphocytes.

Ex Vivo Gene Transfer into Donor Lymphocytes or Spleen Cells

T-cells or splenic lymphocytes from donor mice will be co-cultured with irradiated αGT vector under phosphate depleted conditions or LTKOSN.2 (control VPC for 72 hours at 37° C. in RPMI with 20% FBS and rIL-2. Table N outlines a proposed experiment (Section 7). After retroviral transduction is complete, some of the cells will be split off to determine the vector transduction frequency as outlined in the preliminary data above (Section 4: Specific Aim #1). Cells will also be analyzed by FACS for CD4 and CD8 proportions. Our transduction efficiency will be determined by GFP positive screening.

TABLE N

In Vivo Induction of α(1,3)GT Vector Transduced Lymphocytes

| Number of Cells | DCN Dose | Day 0 | Day 2 | Day 4 | Day 7 | Day 10 | Day 15 | Day 20 |
|---|---|---|---|---|---|---|---|---|
| 1 × 10⁸ | 0 | 3 | 3 | 3 | 3 | 3 | 3 | 3 |
| 1 × 10⁸ | 0.1 | 3 | 3 | 3 | 3 | 3 | 3 | 3 |
| 1 × 10⁸ | 0.2 | 3 | 3 | 3 | 3 | 3 | 3 | 3 |
| 5 × 10⁸ | 0 | 3 | 3 | 3 | 3 | 3 | 3 | 3 |
| 5 × 10⁸ | 0.1 | 3 | 3 | 3 | 3 | 3 | 3 | 3 |
| 5 × 10⁸ | 0.2 | 3 | 3 | 3 | 3 | 3 | 3 | 3 |
| *5 × 10⁸ | 0 | 3 | 3 | 3 | 3 | 3 | 3 | 3 |
| *5 × 10⁸ | 0.1 | 2 | 2 | 2 | 2 | 2 | 2 | 2 |
| *5 × 10⁸ | 0.2 | 2 | 2 | 2 | 2 | 2 | 2 | 2 |

All lymphocyte infusions administered by tail vein injection on day 1 in 100 μHBSS.
*negative control cells transduced with LYTKOSN vector.
DCN administered daily @ 0.1 or 0.2 mg in 1 ml HBSSIP
Blood samples will be analyzed by FACS for GFP fluorescence and lectin binding

Example 17

Tumor Specific Promoters Useful for Ex Vivo Protocals of Invention

The following is nonexclusive list of tumor specific promoters suitable for practice of the invention, given by Genbank accession numbers or patent numbers the disclosures of which are expressly incorporated by reference.

HSU24128 *Human prohormone* convertase (PC1/3) gene, R73368519-73377389-/gopherlib/data/db/.genbank-92/gbpri.seq:

HUMPRDA1A *Homo sapiens* PRAD1/cyclin D1 proto-oncogene, promoterR131139159-131144243-/gopherlib/data/db/.genbank-92/gbpri.seq:

MMTIMP3MI *M.musculus* (Balb/C) TIMP-3 gene for metalloproteinase-3tissue R21667172-21676635-/gopherlib/data/db/. genbank-92/gbrod.seq:S76735

HrMA4 alpha=muscle-specific actin {promoter} [HalocynthiaR91434337-91436077-/gopherlib/data/db/.genbank-92/gbinv.seq:

SPU16263 *Strongylocentrotus purpuratus* cytoplasmic actin I (SpCyI)gene, R94170781-94174495-/gopherlib/data/db/. genbank-92/gbinv.seq:

SUSMSP130A *S.purpuratus* cell surface glycoprotein (msp130) gene, 5'flank andR95059129-95062574-/gopherlib/data/db/. genbank-92/gbinv.seq;:

SUSMSP130B *S.purpuratus* cell surface glycoprotein (msp130) mRNA, 5'end. R95062574-95068440-/gopherlib/data/db/. genbank-92/gbinv.seq:

TBVSG118A *T. brucei* promoter region for variant-specific surfaceglycoproteinR964638—3-96467678-/gopherlib/data/db/. genbank-92/gbinv.seq:

BTU15731 Bos taurus somatotropin receptor gene, exon 1 and liver-specificR8476848-8482291-/gopherlib/data/db/. genbank-92/gbmam.seq gopher.nih.gov:0gb:

DOGCAMII Dog gene for calmodulin, exon 1.R10631174-10634811-/gopherlib/data/db/. genbank-92/gbmam.seq:

LC15LOPRO L.cuniculus 15-lipoxygenase gene, promoter regionR12667022-12669806-/gopherlib/data/db/.genbank-92/gbmam.seq:

MDU32208 Monodelphis domestica ubiquitin C-terminal hydrolase(PGP9.5) gene,R12823493-12828679-/gopherlib/data/db/. genbank-92/gbmam.seq:

OALGB Ovis aries beta-lactoglobulin gene.R14266321-14279312-/gopherlib/data/db/. genbank-92/gbmam.seq:

OCKK3 O.cuniculus keratin K3 gene R15952615-15964713-/gopherlib/data/db/. genbank-92/gbmam.seq:

RAB15LOX Rabbit erythroid cell-specific 15-lipoxygenase (15-lox)gene, R19673279-19689638-/gopherlib/data/db/. genbank-92/gbmam.seq RABSURFA Rabbit lung surfactant protein A related gene, complete gene andR22419294-22432460-/gopherlib/data/db/. genbank-92/gbmam.seq:S55298

LINE/c-MYC {junction sequence} [dogs, transmissible venereal:S64695 luteinizing hormone beta-subunit [sheep, Genomic, 1779 nt].R23183638-23187681-/gopherlib/data/db/. genbank-92/gbmam.seq:S65740 K3 keratin [rabbits, Genomic, 6045 nt].R23217050-23227115-/gopherlib/data/db/. genbank-92/gbmam.seq:

SSIKBAG S.scrofa IkBa gene (promoter region.R25337255-25341446-/gopherlib/data/db/. genbank-92/gbmam.seq:

A08215 Patatin gene and promoter sequence.R4651664-4655250-/gopherlib/data/db/. genbank-92/gbpat.seq:

Promoter region proteinase gene from pSKIII.R9571009-9572031-/gopherlib/data/db/. genbank-92/gbpat.seq:A18399 tac promoter and PhoA signal sequence.R11170222-11171269-/gopherlib/data/db/. genbank-92/gbpat.seq0gb:A23331 T72 gene, TATA box and promoter.R13675642-13681547-/gopherlib/data/db/. genbank-92/gbpat.seq:A23332 T42 gene, TATA box and promoter.R13681547-13685867-/gopherlib/data/db/. genbank-92/gbpat.seq:A23333 E1 gene, TATA box and promoter.R13685867-13690139-/gopherlib/data/db/. genbank-92/gbpat.seq:I02355 Sequence 1 from U.S. Pat. No. 4,518,690.R16695383-16696343-/gopherlib/data/db/. genbank-92/gbpat.seq:I11774 Sequence 1 from U.S. Pat. No. 5,412,085.R23440237-23444507-/gopherlib/data/db/. genbank-92/gbpat.seq:I11775 Sequence 2 from U.S. Pat. No. 5,412,085.R23444507-23445241-/gopherlib/data/db/. genbank-92/gbpat.seq:I11776 Sequence 3 from U.S. Pat. No. 5,412,085.R23445241-23446310-/gopherlib/data/db/. genbank-92/gbpat.seq:I11777 Sequence 4 from U.S. Pat. No. 5,412,085.R23446310-23447422-/gopherlib/data/db/. genbank-92/gbpat.seq:I11778 Sequence 5 from U.S. Pat. No. 5,412,085.R23447422-23448640-/gopherlib/data/db/. genbank-92/gbpat.seq:I11779 Sequence 6 from U.S. Pat. No. 5,412,085.R23448640-23450022-/gopherlib/data/db/. genbank-92/gbpat.seq:I11780 Sequence 7 from U.S. Pat. No. 5,412,085.R23450022-23452658-/gopherlib/data/db/. genbank-92/gbpat.seq:I11781 Sequence 8 from U.S. Pat. No. 5,412,085.R23452658-23456693-/gopherlib/data/db/. genbank-92/gbpat.seq DEECSP sorbitol-6-phosphate 2-dehydrogenase (EC 1.1.1.140) -R1427901-1430273-/gopherlib/data/db/.pir-47/pirl. dat gopher.nih.gov 70

DEHULC L-lactate dehydrogenase (EC 1.1.1.27) chain X—human R1486759-1489842-/gopherlib/data/db/.pir-47/pirl.dat gopher.nih.gov 70

:DEMSLC L-lactate dehydrogenase (EC 1.1.1.27) chain X—mouse R1489842-1494839-/gopherlib/data/db/.pir-47/pirl.dat gopher.nih.gov 70

RDHYE hydroxymethylglutaryl-CoA reductase (NADPH) (EC 1.1.1.34) -R1550326-1555786-/gopherlib/data/db/.pir-47/pirl. dat gopher.nih.gov 70

DERTMX malate dehydrogenase (oxaloacetate-decarboxylating) (NADP+)R1558055-1561973-/gopherlib/data/db/. pir-47/pirl.dat gopher.nih.gov 70

DEFBC cinnamyl-alcohol dehydrogenase (EC 1.1.1.195) —kidney bean R1567549-1570068-/gopherlib/data/db/.pir-47/pirl. dat gopher.nih.gov 70

DCBYIS isocitrate dehydrogenase (NADP+) (EC 1.1.1.42) precursor, R1575149-1577791-/gopherlib/data/db/.pir-47/pirl.dat gopher.nih.gov 70

DERTH1 3beta-hydroxy-Delta5-steroid dehydrogenase multifunctional R1638401-1642033-/gopherlib/data/db/.pir-47/pirl.dat gopher.nih.gov 70

DERTH2 3beta-hydroxy-Delta5-steroid dehydrogenase multifunctional R1642033-1645092-/gopherlib/data/db/.pir-47/pirl.dat gopher.nih.gov 70

:DERTHM 3beta-hydroxy-Delta5-steroid dehydrogenase multifunctional R1645092-1647682-/gopherlib/data/db/.pir-47/pirl.dat gopher.nih.gov 70

DEECIP IMP dehydrogenase (EC 1.1.1.205) - Escherichia coliR1661203-1664039-/gopherlib/data/db/.pir-47/pirl.dat gopher.nih.gov A35029 t-plasminogen activator (EC 3.4.21.68) precursor —rat R8768982-8773280-/gopherlib/data/db/.pir-47/pir2.dat gopher.nih.gov 70

JN0835 carbonate dehydratase (EC 4.2.1.1) I—chimpanzee R10978238-10980068-/gopherlib/data/db/.pir-47/pir2.dat gopher.nih.gov70

JN0836 carbonate dehydratase (EC 4.2.1.1) I—gorilla R10980068-10981891-/gopherlib/data/db/.pir-47/pir2.dat gopher.nih.gov angiotensin precursor—humanR12316682-12319301-/gopherlib/data/db/. pir-47/pir2.dat gopher.nih.gov70 placental lactogen II precursor—mouseR14037523-14040099-/gopherlib/data/db/. pir-47/pir2.dat gopher.nih.gov70 interferon-related protein TIS7—mouseR15017615-15019579-/gopherlib/data/db/. pir-47/pir2.dat gopher.nih.gov70 myelomonocytic growth factor precursor—chicken R15030243-15032831-/gopherlib/data/db/.pir-47/pir2.dat gopher.nih.gov70 immediate-early serum-responsive protein JE—rat R15155748-15158087-/gopherlib/data/db/.pir-47/pir2.dat gopher.nih.gov70

T-cell activation protein precursor—human R15159869-15162847-/gopherlib/data/db/. pir-47/pir2.dat gopher.nih.gov70 tumor necrosis factor receptor type 2 precursor -mouseR15285255-15288298-/gopherlib/data/db/. pir-47/pir2.dat gopher.nih.gov 70

Ly-6.2 protein precursor—mouse R18016944-18020231-/gopherlib/data/db/. pir-47/pir2.dat gopher.nih.gov70

H-2 class I histocompatibility antigen D-q—mouse (fragment) R18119719-18121300-/gopherlib/data/db/. pir-47/pir2.datgopher.nih.gov 7

H-2 class I histocompatibility antigen L-q—mouse (fragment) R18124642-18126223-/gopherlib/data/db/.pir-47/pir2.dat gopher.nih.gov 70 carcinoembryonic antigen precursor—humanR18760124-18767388-/gopherlib/data/db/. pir-47/pir2.dat gopher.nih.gov70 histone H2A, testis—ratR19530794-19532091-/gopherlib/data/db/. pir-47/pir2.dat gopher.nih.gov7 proliferating cell nuclear antigen—fruit fly (DrosophilaR19937461-19940119-/gopherlib/data/db/.pir-47/pir2.dat gopher.nih.gov 70 collagen alpha 1(II) chain—golden hamster (fragments) R20906501-20908556-/gopherlib/data/db/.pir-47/pir2.dat gopher.nih.gov 70 lipid-binding protein, keratinocyte—mouse R23701052-23702497-/gopherlib/data/db/. pir-47/pir2.dat gopher.nih.gov70 glycophorin A precursor (blood group M)—human R24944830-24949396-/gopherlib/data/db/.pir-47/pir2.dat gopher.nih.gov70 cell surface glycoprotein CD11a precursor—human R25264896-25270650-/gopherlib/data/db/.pir-47/pir2.dat gopher.nih.gov70 thyroid hormone receptor beta-1—mouse R25805198-25807750-/gopherlib/data/db/. pir-47/pir2.dat gopher.nih.gov70 beta-microseminoprotein precursor—human R25899124-25903398-/gopherlib/data/db/. pir-47/pir2.dat gopher.nih.gov70 homeotic protein Hox 1.4—mouse R26754180-26757218-/gopherlib/data/db/. pir-47/pir2.dat gopher.nih.gov70

MTV-3 protein—mouse mammary tumor virus (provirus) R32101429-32103143-/gopherlib/data/db/.pir-47/pir2.dat gopher.nih.gov70

MTV-13 protein—mouse mammary tumor virus (provirus) R32103143-32104859-/gopherlib/data/db/.pir-47/pir2.dat gopher.nih.gov 70

MTV-1/MTV-6 protein—mouse mammary tumor virus (provirus)R32107451-32109190-/gopherlib/data/db/.pir-47/pir2.dat gopher.nih.gov 70 segment S5 protein—wound tumor virus R33159190-33162079-/gopherlib/data/db/. pir-47/pir2.dat gopher.nih.

glycoprotein gp100 precursor, melanocyte lineage—human R97214013-97217151-/gopherlib/data/db/.pir-47/pir2.dat gopher.nih.gov 70 heregulin-alpha precursor—humanR97490681-97493391-/gopherlib/data/db/. pir-47/pir2.dat gopher.nih.gov 70 lactose synthase (EC 2.4.1.22)—human R99350057-99352224-/gopherlib/data/db/. pir-47/pir2.dat gopher.nih.gov 70 melanoma antigen-specific T-cell receptor alpha chain (V-J-CR99750100-99751442-/gopherlib/data/db/.pir-47/pir2.dat gopher.nih.gov 70 melanoma antigen-specific T-cell receptor alpha chain (V-J-CR99751442-99752781-/gopherlib/data/db/.pir-47/pir2.dat gopher.nih.gov 70 melanoma antigen-specific T-cell receptor alpha chain (V-J-CR99752781-99754077-/gopherlib/data/db/.pir-47/pir2.dat gopher.nih.gov 70 melanoma antigen-specific T-cell receptor alpha chain (V-J-CR99754077-99755382-/gopherlib/data/db/.pir-47/pir2.dat gopher.nih.gov 70 melanoma antigen-specific T-cell receptor alpha chain (V-J-CR99755382-99756680-/gopherlib/data/db/.pir-47/pir2.dat gopher.nih.gov 70 melanoma antigen-specific T-cell receptor beta chain (V-J-CR99756680-99758027-/gopherlib/data/db/. pir-47/pir2.dat gopher.nih.gov 70 melanoma antigen-specific T-cell receptor beta chain (V-J-CR99758027-99759369-/gopherlib/data/db/.pir-47/pir2.dat gopher.nih.gov 70 melanoma antigen-specific T-cell receptor beta chain (V-J-CR99759369-99760671-/gopherlib/data/db/. pir-47/pir2.dat gopher.nih.gov 70 melanoma antigen-specific T-cell receptor beta chain (V-J-CR99760671-99762021-/gopherlib/data/db/. pir-47/pir2.dat gopher.nih.gov 70 melanoma-associated antigen CD63—human R99762021-99766947-/gopherlib/data/db/.pir-47/pir2.dat gopher.nih.gov 70

As can be seen from the foregoing, the invention accomplishes at least all of its objectives.

What is claimed is:

1. A method of selectively targeting and killing tumor cells comprising:

transforming said tumor cells with a polynucleotide sequence that comprises a tetracycline-controlled transactivator responsive promoter whereby the expression of said polynucleotide sequence creates a galactosyl epitope, and exposing said transformed tumor cells to human serum so that said cells are killed by complement mediated destruction.

2. The method of claim 1 wherein said polynucleotide sequence is murine $\alpha 1,3$ galactosyl transferase.

3. A method of selectively targeting and killing tumor cells comprising:

transducing said tumor cells with a polynucleotide sequence that comprises a recombinant retroviral or adenoviral vector whereby the expression of said polynucleotide sequence creates a galactosyl epitope, and exposing said transformed tumor cells to human serum so that said cells are killed by complement mediated destruction.

4. A method of selectively targeting and killing tumor cells comprising:

transforming by delivering to said tumor cells a vector producer cell line with a polynucleotide sequence that comprises a recombinant mini-viral Herpes Simplex Virus plasmid vector whereby the expression of said polynucleotide sequence creates a galactosyl epitope, and exposing said transformed tumor cells to human serum so that said cells are killed by complement mediated destruction.

5. The method of claim 4 wherein said vector producer cell line does not contain an active murine $\alpha 1,3$ galactosyl transferase gene.

6. The method of claim 4 wherein said vector comprises:

a replication origin, "ori S" from Herpes Simplex Virus;

a Herpes Simplex Virus packaging sequence "a"

an Epstein-Barr virus nucleic antigen gene "EBNA-1";

an Epstein-Barr virus latent origin of replication; and a transcription unit sequence encoding an $\alpha(1,3)$ galactosyl transferase.

7. The method of claim 6 wherein said transcription unit comprises an inducible promoter.

8. A recombinant mini-viral Herpes Simplex Virus plasmid vector comprising:

a replication origin, "ori S" from Herpes Simplex Virus;

a Herpes Simplex Virus packaging sequence "a"

an Epstein-Barr virus nucleic antigen gene "EBNA-1";

an Epstein-Barr virus latent origin of replication; and a transcription unit sequence encoding an active galactosyl epitope.

9. The vector of claim 8 further comprising a transcription unit for expression of a galactosyl epitope.

10. The vector of claim 9 wherein said galactosyl epitope is murine $\alpha 1,3$ galactosyl transferase.

11. The vector of claim 9 wherein said transcription unit comprises an inducible promoter.

12. A method of killing tumor cells comprising:

transforming said tumor cells with a polynucleotide sequence which encodes an enzyme which causes the formation of galactosyl epitope the expression of which is regulated by a tetracycline controlled transactivator responsive promoter;

inducing said promoter to cause expression of said galactosyl epitope; and exposing said transformed cells to human serum.

13. The method of claim 12 wherein said galactosyl epitope is murine $\alpha 1,3$ galactosyl transferase.

14. A method of killing tumor cells comprising:

transforming said tumor cells with a polynucleotide sequence which encodes an enzyme which causes the formation of galactosyl epitope the expression of which is regulated by a doxycycline inducible tetracycline controlled transactivator responsive promoter.

* * * * *